(12) United States Patent
Biedermann et al.

(10) Patent No.: US 9,381,043 B2
(45) Date of Patent: Jul. 5, 2016

(54) INSERT FOR A TOOL FOR ASSEMBLING A BONE ANCHORING DEVICE AND TOOL FOR ASSEMBLING A BONE ANCHORING DEVICE

(75) Inventors: Lutz Biedermann, VS-Villingen (DE); Wilfried Matthis, Weisweil (DE); Berthold Dannecker, Georgen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 884 days.

(21) Appl. No.: 13/462,697

(22) Filed: May 2, 2012

(65) Prior Publication Data

US 2012/0283032 A1    Nov. 8, 2012

Related U.S. Application Data

(60) Provisional application No. 61/525,090, filed on Aug. 18, 2011.

(30) Foreign Application Priority Data

May 2, 2011    (JP) .................................. 2011-102944
Aug. 18, 2011    (EP) ..................................... 11178036

(51) Int. Cl.
*A61B 17/70*    (2006.01)
*A61B 17/86*    (2006.01)
(Continued)

(52) U.S. Cl.
CPC ......... *A61B 17/7037* (2013.01); *A61B 17/7074* (2013.01); *A61B 17/8685* (2013.01);
(Continued)

(58) Field of Classification Search
CPC ............ B27B 27/00; B27B 9/00; B27B 27/02
USPC .................... 29/244, 255, 253, 265, 270, 278
See application file for complete search history.

(56) References Cited

U.S. PATENT DOCUMENTS

| 2,408,560 A | 10/1946 | Keehn |
| 3,713,198 A | 1/1973 | Tobak et al. |

(Continued)

FOREIGN PATENT DOCUMENTS

| EP | 2 022 423 A1 | 2/2009 |
| EP | 2 191 780 A1 | 6/2010 |

(Continued)

OTHER PUBLICATIONS

Extended European Search Report for European Application No. 11178036.7, extended European Search Report dated Oct. 25, 2011 and mailed Nov. 2, 2011 (7 pgs.).

(Continued)

*Primary Examiner* — Lee D Wilson
(74) *Attorney, Agent, or Firm* — Lewis Roca Rothgerber Christie LLP

(57) ABSTRACT

An insert for a tool for assembling a bone anchoring device including a bone anchoring element with a head and a shaft to be anchored in bone and a receiving part, the insert configured for insertion into a holder of the tool, the insert including an elongate body with a longitudinal axis, wherein a first recess configured to receive a shaft of a bone anchoring element extends on a surface of the elongate body along the longitudinal axis, has a first diameter, and is oriented towards a first radial direction relative to the longitudinal axis, wherein a second recess configured to receive a shaft of a bone anchoring element extends on a surface of the elongate body along the longitudinal axis, has a second diameter greater than the first diameter, and is oriented towards a second radial direction relative to the longitudinal axis different than the first radial direction.

30 Claims, 19 Drawing Sheets

(51) Int. Cl.
*A61B 17/88* (2006.01)
*A61B 17/00* (2006.01)

(52) U.S. Cl.
CPC ............. *A61B17/88* (2013.01); *A61B 17/7032* (2013.01); *A61B 17/866* (2013.01); *A61B 2017/00526* (2013.01); *Y10T 29/49876* (2015.01); *Y10T 29/49947* (2015.01); *Y10T 29/5397* (2015.01); *Y10T 29/53678* (2015.01); *Y10T 29/53796* (2015.01); *Y10T 29/53974* (2015.01); *Y10T 29/53978* (2015.01)

(56) References Cited

U.S. PATENT DOCUMENTS

| | | | |
|---|---|---|---|
| 3,810,293 A | 5/1974 | Tobak et al. | |
| 5,782,831 A | 7/1998 | Sherman et al. | |
| 6,050,997 A | 4/2000 | Mullane | |
| 6,251,111 B1 | 6/2001 | Barker et al. | |
| 6,623,485 B2 | 9/2003 | Doubler et al. | |
| 6,637,295 B2 * | 10/2003 | Weaver | 81/3.29 |
| 6,964,665 B2 | 11/2005 | Thomas et al. | |
| 7,073,415 B2 | 7/2006 | Casutt et al. | |
| 7,105,029 B2 | 9/2006 | Doubler et al. | |
| 7,335,201 B2 | 2/2008 | Doubler et al. | |
| 7,468,064 B2 | 12/2008 | Bruneau et al. | |
| 7,591,836 B2 | 9/2009 | Dick et al. | |
| 7,665,718 B1 * | 2/2010 | Benson | B25B 27/10 269/237 |
| 7,678,136 B2 | 3/2010 | Doubler et al. | |
| 7,833,251 B1 | 11/2010 | Ahlgren et al. | |
| 7,942,906 B2 | 5/2011 | Bishop | |
| 7,981,143 B2 | 7/2011 | Doubler et al. | |
| 7,988,694 B2 | 8/2011 | Barrus et al. | |
| 8,192,470 B2 | 6/2012 | Biedermann et al. | |
| 8,328,817 B2 | 12/2012 | Strauss | |
| 8,881,358 B2 | 11/2014 | Biedermann et al. | |
| 2001/0005796 A1 | 6/2001 | Zdeblick et al. | |
| 2001/0047173 A1 | 11/2001 | Schlapfer et al. | |
| 2005/0096653 A1 | 5/2005 | Doubler et al. | |
| 2005/0228392 A1 | 10/2005 | Keyer et al. | |
| 2006/0025769 A1 | 2/2006 | Dick et al. | |
| 2006/0200128 A1 | 9/2006 | Mueller | |
| 2006/0243616 A1 | 11/2006 | Caron | |
| 2007/0119871 A1 | 5/2007 | Garcia | |
| 2007/0213722 A1 | 9/2007 | Jones et al. | |
| 2007/0270842 A1 | 11/2007 | Bankoski et al. | |
| 2007/0276379 A1 | 11/2007 | Miller et al. | |
| 2007/0289411 A1 * | 12/2007 | Olaneta Arambarri | 81/3.47 |
| 2008/0009863 A1 | 1/2008 | Bond et al. | |
| 2008/0045950 A1 | 2/2008 | Dewey | |
| 2008/0108992 A1 | 5/2008 | Barry et al. | |
| 2008/0234750 A1 | 9/2008 | Woods et al. | |
| 2009/0036934 A1 | 2/2009 | Biedermann et al. | |
| 2009/0105756 A1 | 4/2009 | Richelsoph | |
| 2009/0149887 A1 | 6/2009 | Schlaepfer et al. | |
| 2009/0157125 A1 | 6/2009 | Hoffman et al. | |
| 2009/0228054 A1 | 9/2009 | Hoffman et al. | |
| 2009/0266728 A1 | 10/2009 | Turner et al. | |
| 2010/0063545 A1 | 3/2010 | Richelsoph | |
| 2010/0076490 A1 | 3/2010 | Greenwald et al. | |
| 2010/0137875 A1 | 6/2010 | Marino et al. | |
| 2010/0137915 A1 | 6/2010 | Anderson et al. | |
| 2010/0160975 A1 | 6/2010 | Biedermann et al. | |
| 2010/0160976 A1 | 6/2010 | Biedermann et al. | |
| 2010/0168800 A1 | 7/2010 | Biedermann et al. | |
| 2010/0168801 A1 | 7/2010 | Biedermann et al. | |
| 2011/0276098 A1 | 11/2011 | Biedermann et al. | |
| 2012/0124813 A1 * | 5/2012 | Biedermann et al. | 29/525.01 |
| 2012/0165874 A1 | 6/2012 | Biedermann et al. | |
| 2012/0172932 A1 | 7/2012 | Biedermann et al. | |
| 2012/0179209 A1 | 7/2012 | Biedermann et al. | |
| 2012/0179211 A1 | 7/2012 | Biedermann et al. | |
| 2012/0283032 A1 | 11/2012 | Biedermann et al. | |
| 2012/0283789 A1 | 11/2012 | Biedermann et al. | |

FOREIGN PATENT DOCUMENTS

FR 2 854 143 A1 10/2004
WO WO 2007/038350 A2 4/2007

OTHER PUBLICATIONS

Office action for U.S. Appl. No. 14/508,565, mailed by the USPTO on Dec. 17, 2015 (6 pages).
Office action for U.S. Appl. No. 13/101,997, mailed by the USPTO on Dec. 10, 2013 (12 pages).
Final Rejection for U.S. Appl. No. 13/101,989 mailed by the USPTO on Oct. 10, 2013 (13 pages).
Office action for U.S. Appl. No. 13/101,989 mailed by the USPTO on Jan. 31, 2013 (22 pages).
European Search Report for European Application 10162063.1 in the name of Biedermann Motech GmbH Co. KG, European Search Report dated Jul. 14, 2010 and mailed Jul. 22, 2010 (5 pgs.).
European Search Report for European Application 10162063.1 in the name of Biedermann Motech GmbH & Co. KG, European Search Report dated Oct. 5, 2010 and mailed Oct. 13, 2010 (10 pgs.).
European Search Report for European Application 10192278.9 in the name of Biedermann Motech GmbH, European Search Report dated Feb. 16, 2011 and mailed Feb. 23, 2011 (7 pgs.).

* cited by examiner

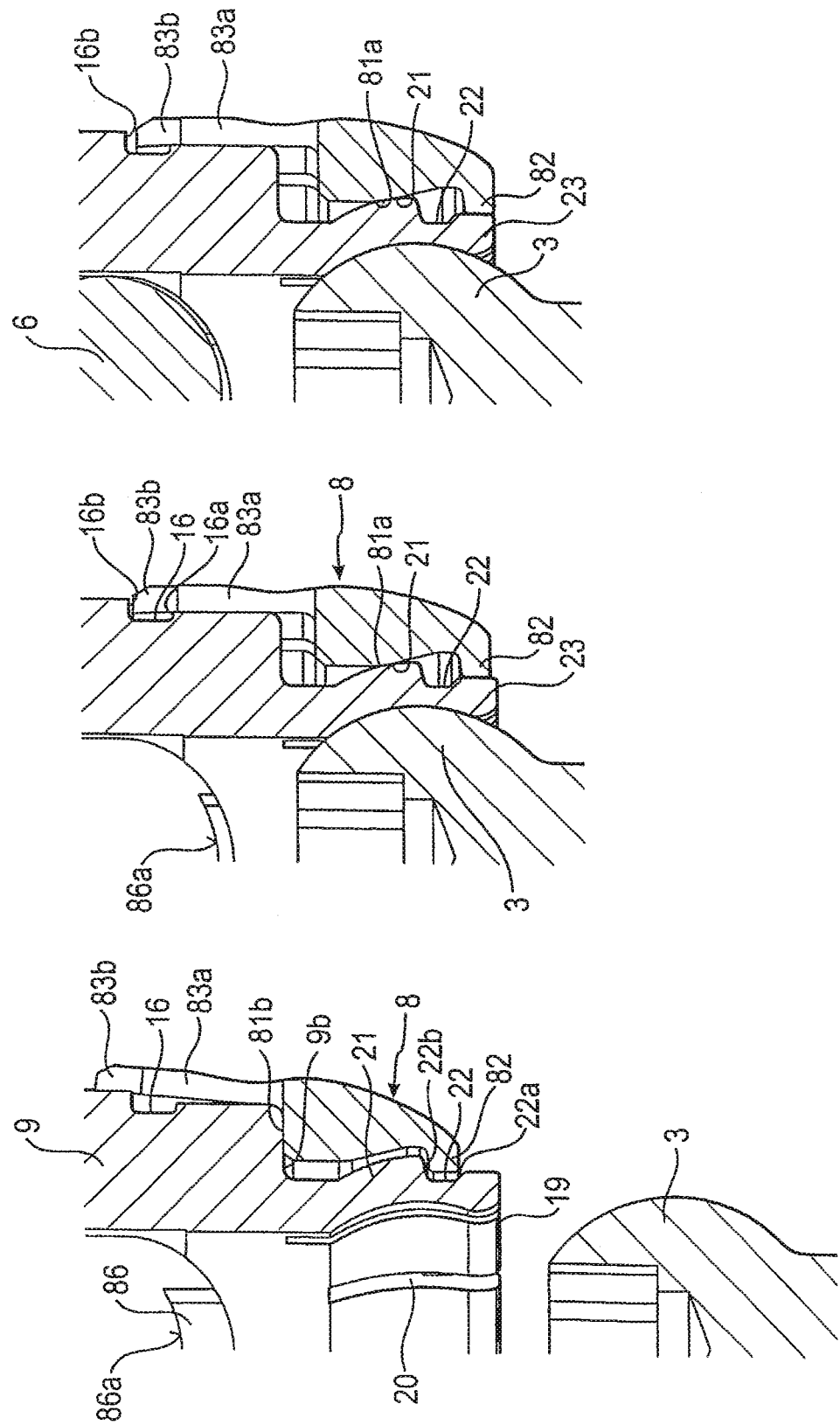

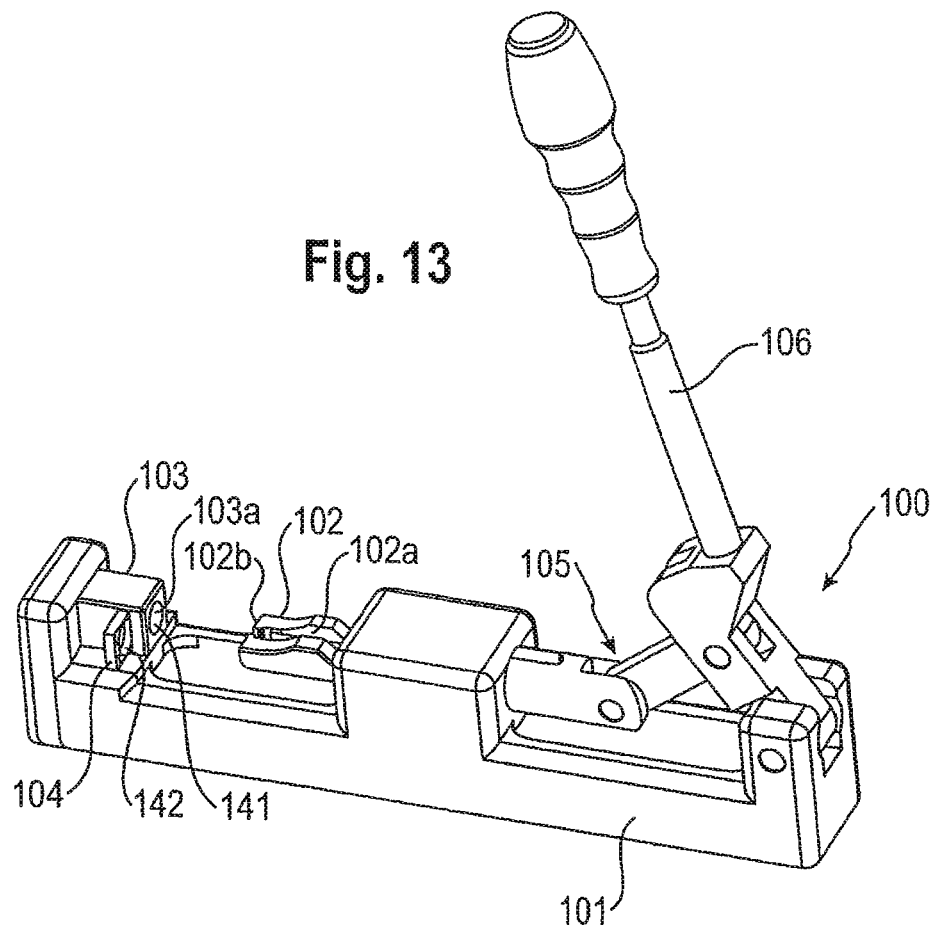
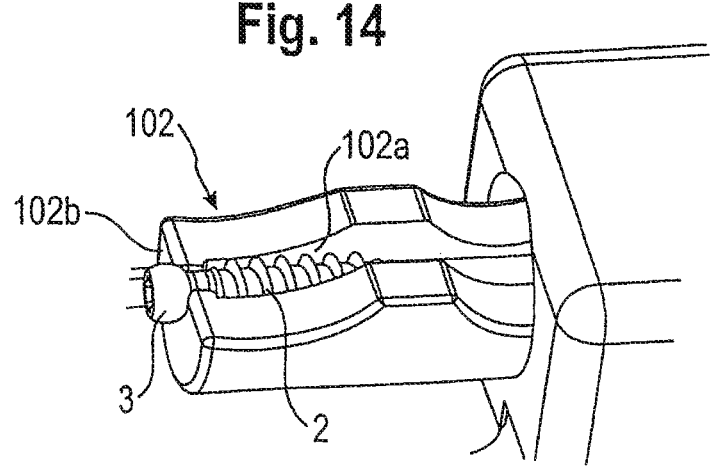

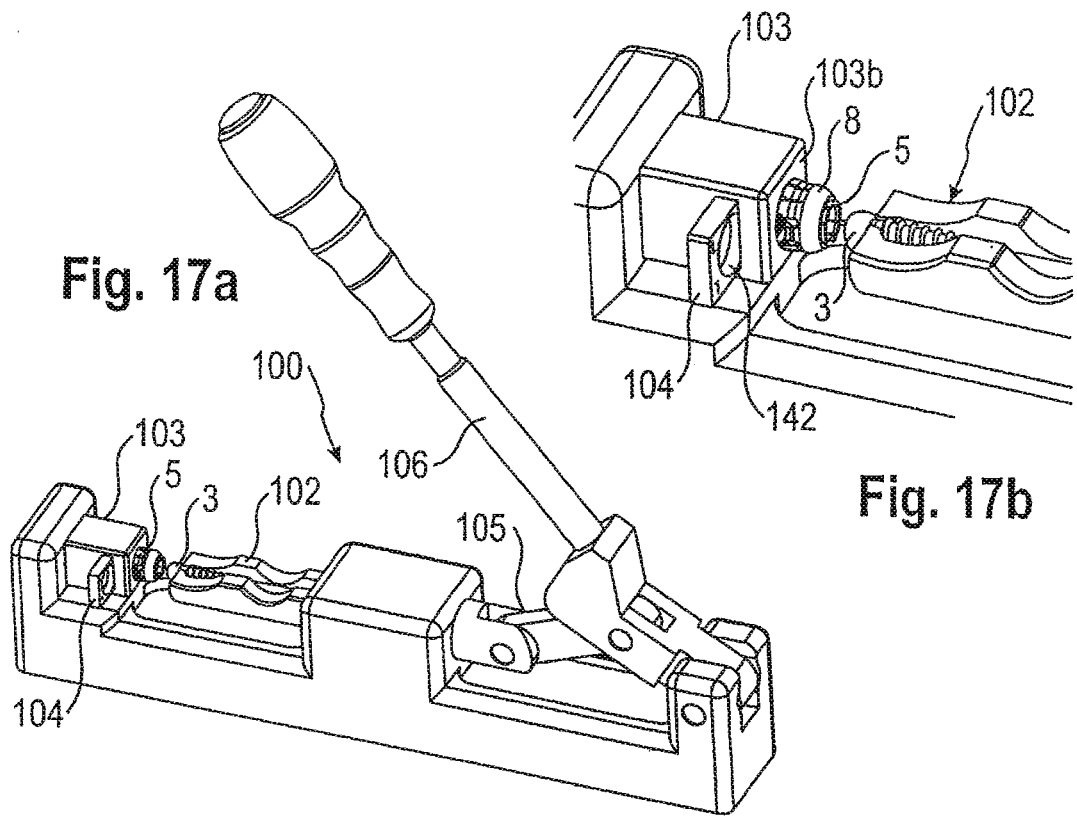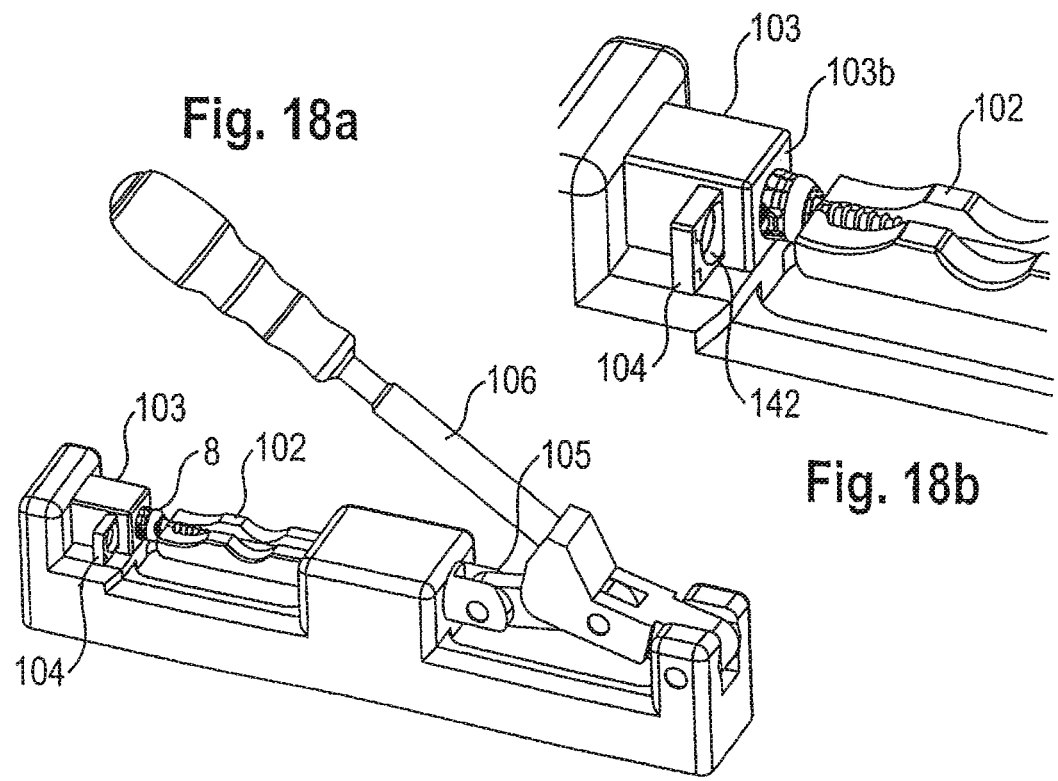

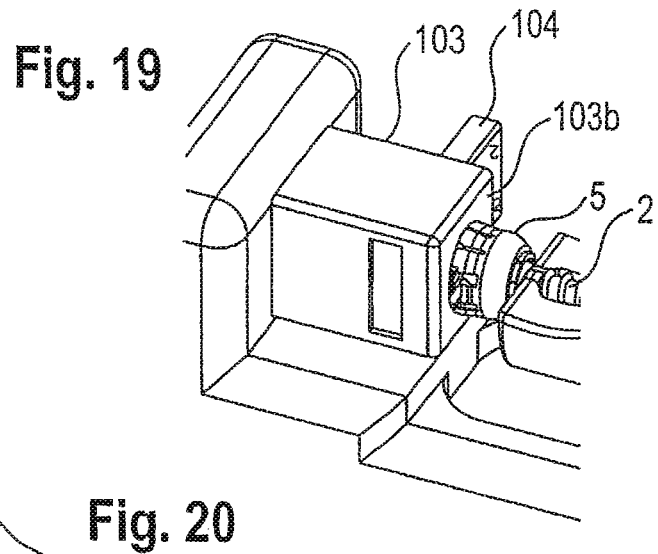
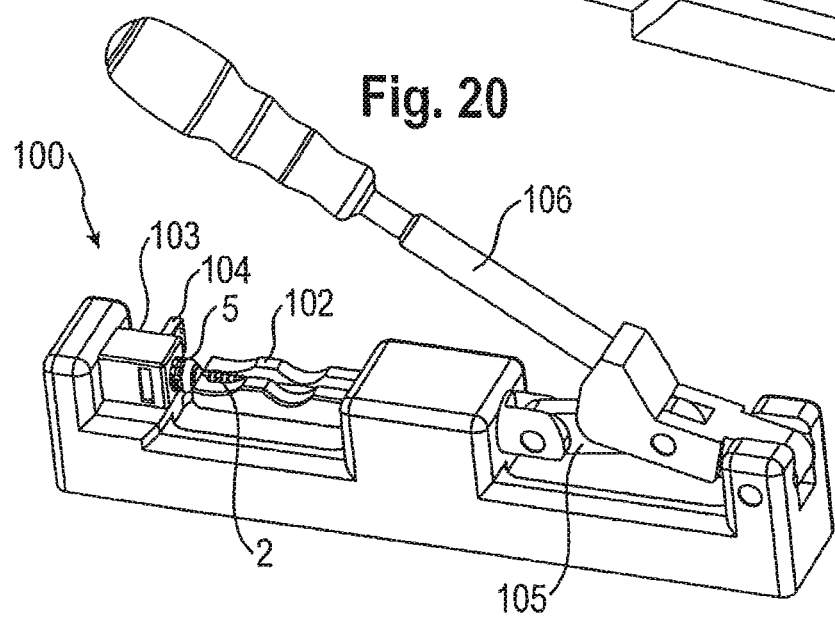
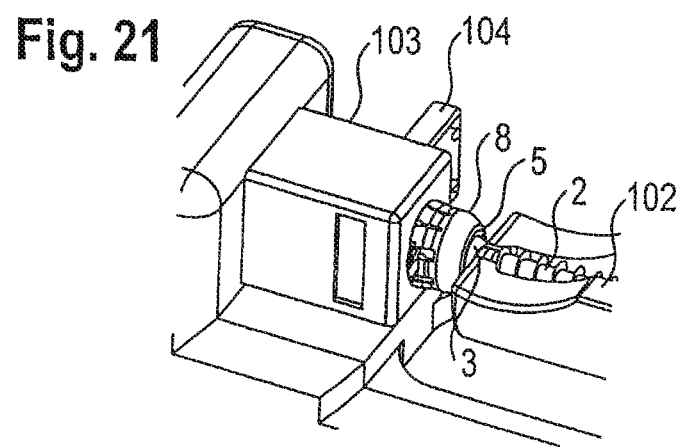

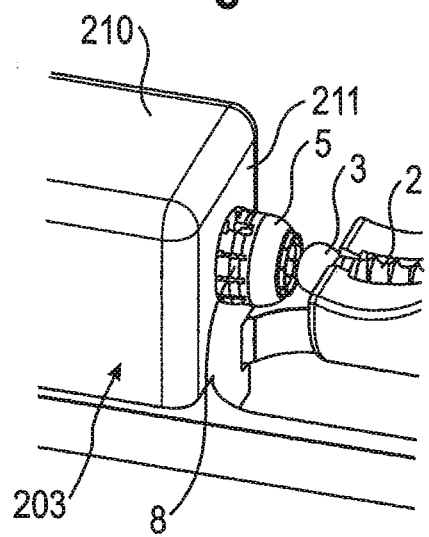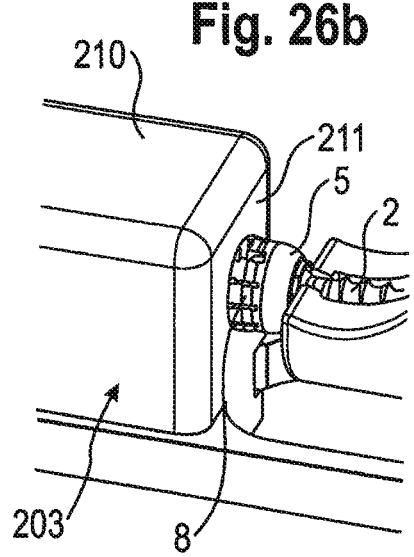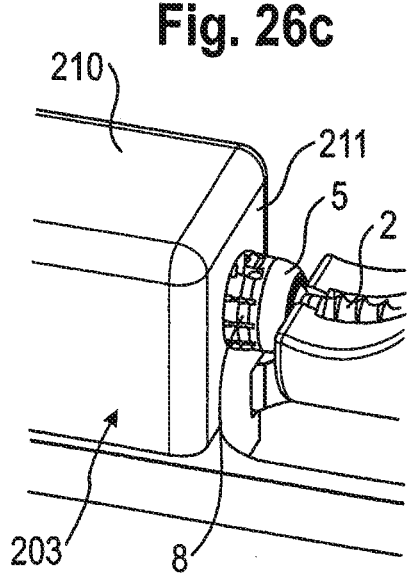

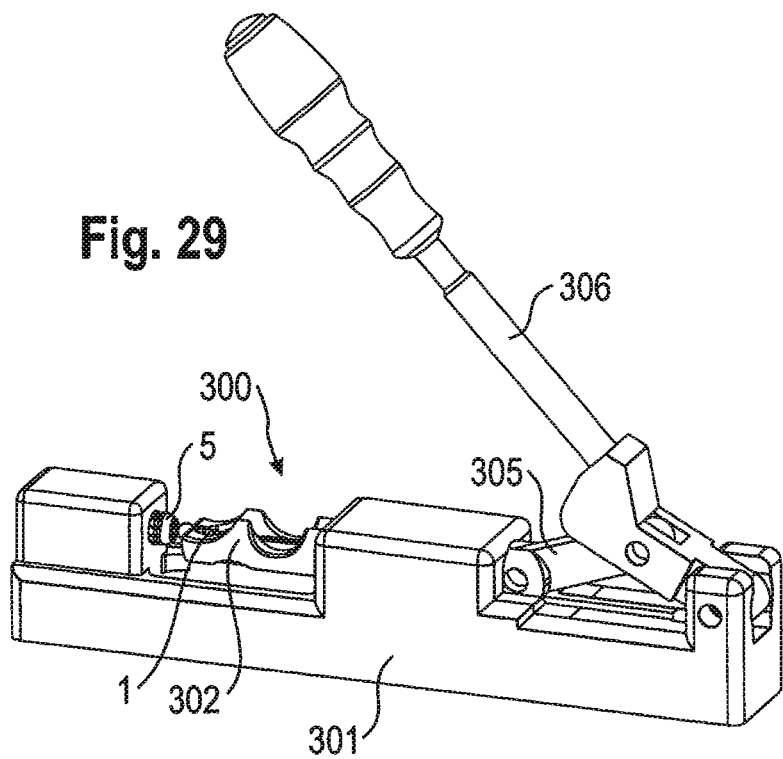
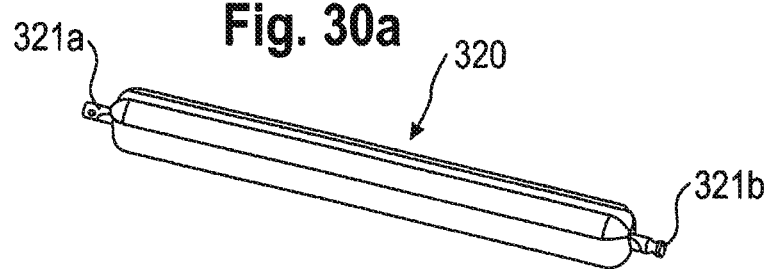
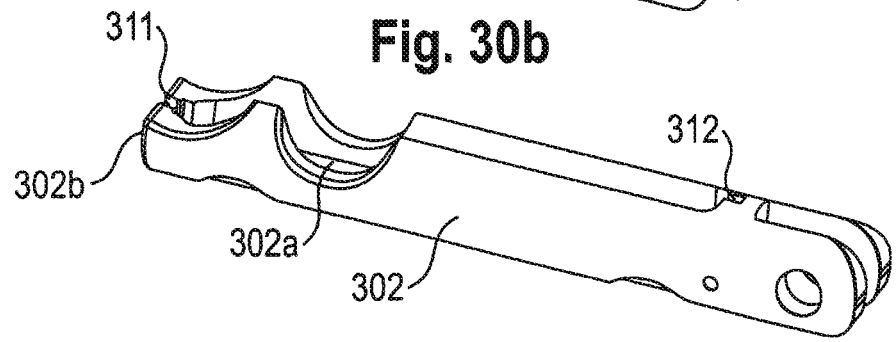

INSERT FOR A TOOL FOR ASSEMBLING A BONE ANCHORING DEVICE AND TOOL FOR ASSEMBLING A BONE ANCHORING DEVICE

CROSS-REFERENCE TO RELATED APPLICATION(S)

The present application claims the benefit of U.S. Provisional Patent Application Ser. No. 61/525,090, filed Aug. 18, 2011, the contents of which are hereby incorporated by reference in their entirety, and claims priority to European Patent Application EP 11 178 036.7, filed Aug. 18, 2011 and Japanese Patent Application JP 2011-102944, filed May 2, 2011 the contents of which are hereby incorporated by reference in their entirety.

BACKGROUND

1. Field of the Invention

The invention relates to an insert for a tool for assembling a bone anchoring device including a bone anchoring element with a head and a shaft to be anchored in bone and a receiving part, and the tool for assembling such a bone anchoring device. The insert is configured to be inserted into a longitudinal recess of a holder of the tool. The insert is capable of receiving the bone anchoring element, and has at least two recesses configured to receive different sized bone anchoring elements.

2. Description of Related Art

WO 2007/038350 A2 discloses an apparatus for connecting a bone anchor to a support rod, the apparatus including a connector body and a cap. The connector body has a socket for insertion, angulation and removal of a bone anchor. A sleeve is provided, which is configured to fit over the connector body in a temporary position, in which the sleeve permits insertion of the bone anchor, to move to a provisional locking position in which the sleeve permits angulation but prevents removal of the bone anchor, and to move to a locking position, in which the sleeve prevents both angulation and removal of the bone anchor.

SUMMARY

If a head of an anchoring element is freely pivotable with respect to a receiving part, alignment of the receiving part and insertion of a rod may be difficult in more complex clinical applications, for example, when multiple bone anchors are to be connected to the rod.

In some instances, there is also a need to have a choice between different anchoring elements during surgery, to select the most appropriate anchoring elements for a specific clinical application.

It is an object of the invention to provide an improved insert for a tool for assembling a bone anchoring device and to provide an improved tool for assembly of such a bone anchoring device.

A receiving part to be used with the tool according to an embodiment of the invention allows insertion of a head of a bone anchoring element into a receiving part body when a locking ring is in a first position which is an insertion position. In this position, the locking ring is latched with respect to the receiving part body. Therefore, the locking ring will not be inadvertently moved to compress a head receiving portion of the receiving part body, in order to facilitate the insertion of the head.

In a second position, which is a pre-locking position, the locking ring is latched with respect to the receiving part body, and the head receiving portion is compressed so that the bone anchoring element is held in an adjustable angular position but is not fully locked. This prevents inadvertent removal of the bone anchoring element and holds the receiving part body in an adjustable angular position with respect to the head of the bone anchoring element. Therefore, safe and convenient handling of the bone anchoring device during surgery can be assured.

In a third position, which is a locking position, the locking ring compresses the head receiving portion such that the bone anchoring element is fully locked and cannot pivot.

The receiving part body and the locking ring may be pre-assembled, and may be delivered after manufacture in a configuration in which the locking ring is latched in the first position to allow introduction of the head of the bone anchoring element. A suitable bone anchoring element, for example, a bone screw with a desired diameter and length, can be selected and inserted into the receiving part. Thereafter, the locking ring can be moved into the second position with respect to the receiving part, where the head is pre-locked. The latching of the locking ring in the receiving part body in the second position may be audible, so that a person who assembles the bone anchoring device can be sure of correct assembly of the bone anchoring element in the receiving part. In the pre-locked condition, the bone anchoring element may only be pivotable with respect to the receiving part by applying an additional force, to overcome the frictional force of the clamping of the head.

With such a bone anchoring device, a modular system can be provided, which allows for combinations of various anchoring elements with any suitable receiving part on demand, depending on the actual clinical requirements. This reduces the costs associated with polyaxial screws, reduces inventory, and gives the surgeon a wide choice of implants.

A method of assembling the bone anchoring device according to embodiments of the invention can be carried out by any specialist, for example, by a surgeon or any personnel assisting him or her before or during surgery.

A tool and an insert according to embodiments of the invention is easy to handle and provides for safer assembly of the bone anchoring device.

BRIEF DESCRIPTION OF THE DRAWINGS

Further features and advantages of the invention will become apparent from the description of embodiments by means of the accompanying drawings. In the drawings:

FIG. 8 shows a cross-sectional view of a portion of the bone anchoring device in a first step of assembly, where a bone anchoring element is going to be inserted into the receiving part;

FIG. 9 shows a cross-sectional view of a portion of the bone anchoring device in a second step of assembly, where a head of the bone anchoring element has been introduced into the receiving part and is pre-locked;

FIG. 10 shows a cross-sectional view of a portion of the bone anchoring device where the head is locked;

FIG. 13 shows a perspective view of a tool for assembling a bone anchoring device according to a first embodiment of the invention;

FIG. 14 shows an enlarged perspective view of a portion of the tool according to the first embodiment, with a bone anchoring element inserted into a holder;

FIG. 17a shows a perspective view of the tool according to the first embodiment depicting a step of assembly, where the head of the bone anchoring element is going to be inserted into the receiving part;

FIG. 17b shows an enlarged view of a portion of FIG. 17a;

FIG. 18a shows a perspective view of the tool according to the first embodiment depicting another step of assembly, with the head of the bone anchoring element inserted into the receiving part;

FIG. 18b shows an enlarged portion of FIG. 18a;

FIG. 19 shows an enlarged perspective view of a portion of the tool according to the first embodiment with the bone anchoring device after insertion of the head and before entering the pre-locking position;

FIG. 20 shows a perspective view of the tool according to the first embodiment with the bone anchoring device in the pre-locking position;

FIG. 21 shows a perspective view of an enlarged portion of the tool according to the first embodiment, where the locking ring of the bone anchoring device has assumed the pre-locking position and clamps the head;

FIG. 26a shows a perspective view of a portion of the tool in a first position of use according to the second embodiment;

FIG. 26b shows a perspective view of a portion of the tool in a second position of use according to the second embodiment;

FIG. 26c shows a perspective view of a portion of the tool in a third position of use according to the second embodiment;

FIG. 29 shows a perspective view of a tool according to a third embodiment of the invention, depicting a step of assembly where the head of the bone anchoring element is to be inserted into the receiving part;

FIG. 30a shows a perspective view of an insert for a first holder according to the third embodiment, in the form of a cylindrical section having several cylinder-shaped or U-shaped recesses;

FIG. 30b shows a perspective view of a first holder according to the third embodiment;

DETAILED DESCRIPTION

Figure 1:
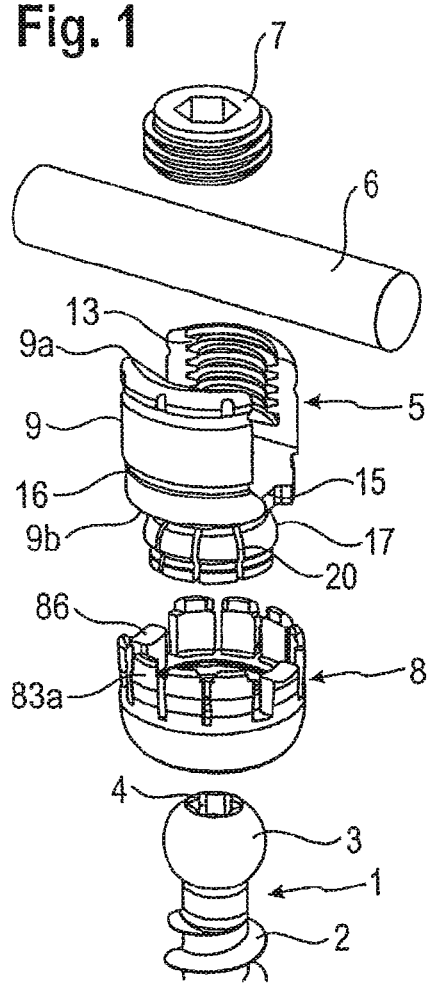
FIG. 1 shows a perspective exploded view of a bone anchoring device according to an embodiment of the invention.
Figure 2:
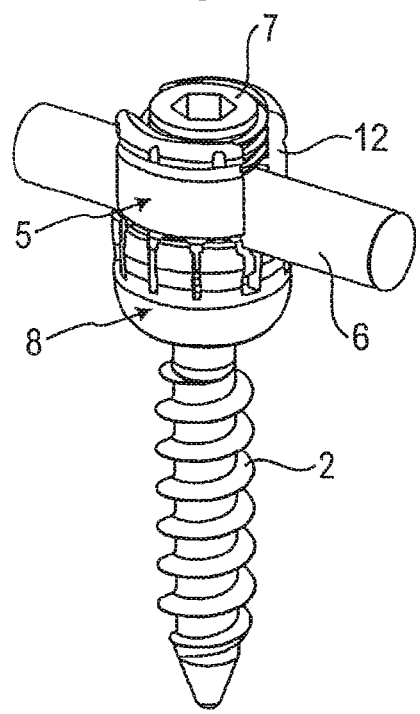
FIG. 2 shows a perspective view of the bone anchoring device of FIG. 1 in an assembled state.
Figure 3:
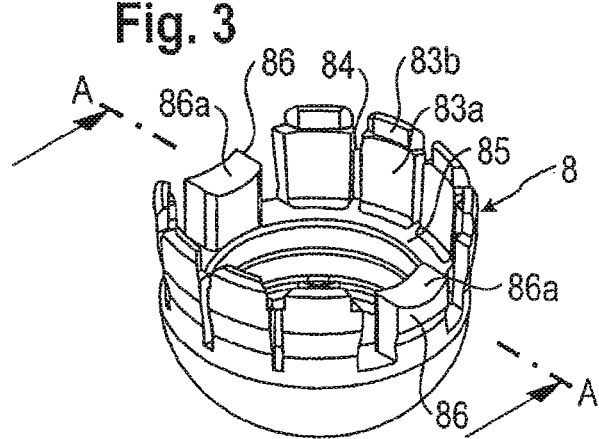
FIG. 3 shows an enlarged perspective view of a locking ring according to an embodiment of the invention.
Figure 4:
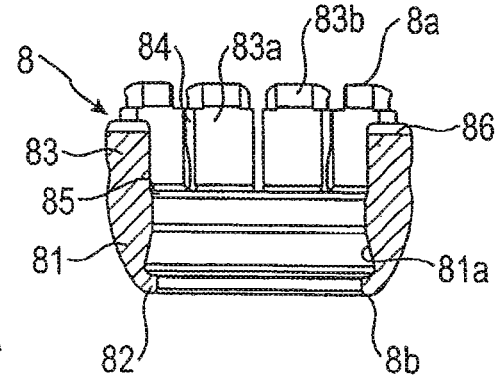
FIG. 4 shows a cross-sectional view of the locking ring shown in FIG. 3 along line A-A in FIG. 3.

As shown in FIGS. 1 to 7, a bone anchoring device according to an embodiment of the invention includes a bone anchoring element 1 in the form of a bone screw having a threaded shaft 2 and a head 3 with a curved surface portion. In this embodiment the head 3 is spherical segment-shaped. The head 3 has a recess 4 for engagement with a tool. The bone anchoring device also includes a receiving part body 5 for receiving a rod 6 to connect it to the bone anchoring element 1. Further, a fixation element 7 in the form of an inner screw is provided for fixing the rod 6 in the receiving part body 5. The bone anchoring device also includes a locking ring 8 for locking the head 3 in the receiving part body 5.

Figure 7:
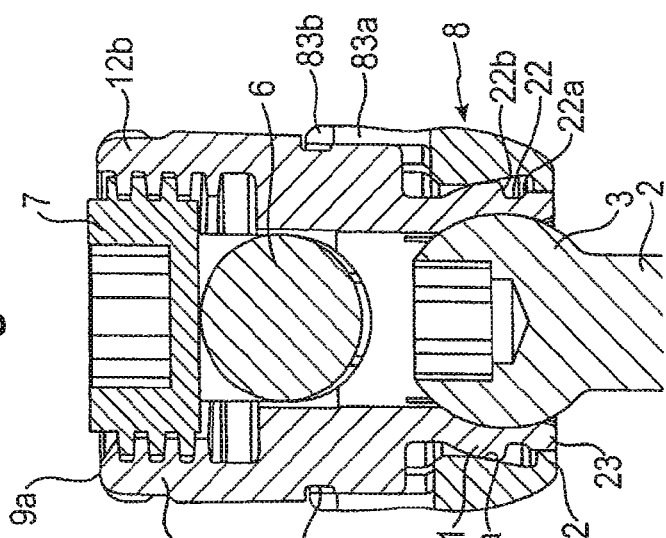
FIG. 7 shows a cross-sectional view of the bone anchoring device in an assembled state, with a rod inserted and fixed, the section being taken in a plane perpendicular to the rod axis, and wherein the locking ring is in a third position.
Figure 6:
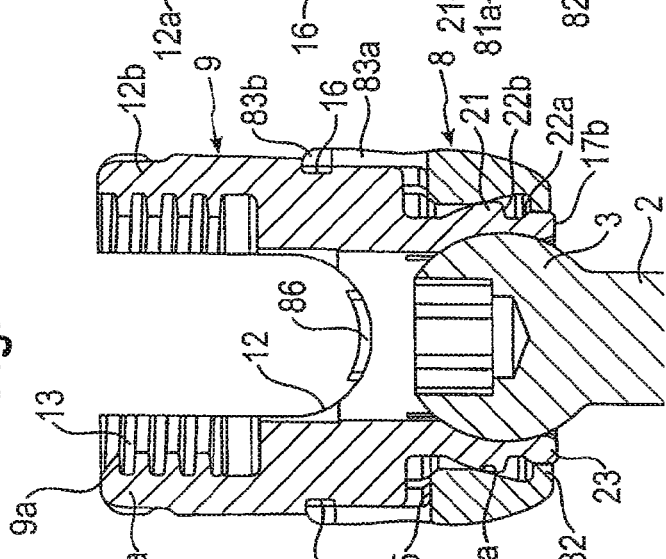
FIG. 6 shows a cross-sectional view of the bone anchoring device in an assembled state, the section being taken in a plane perpendicular to the rod axis, where the locking ring is in a second position and is latched with respect to the receiving part body.
Figure 5:
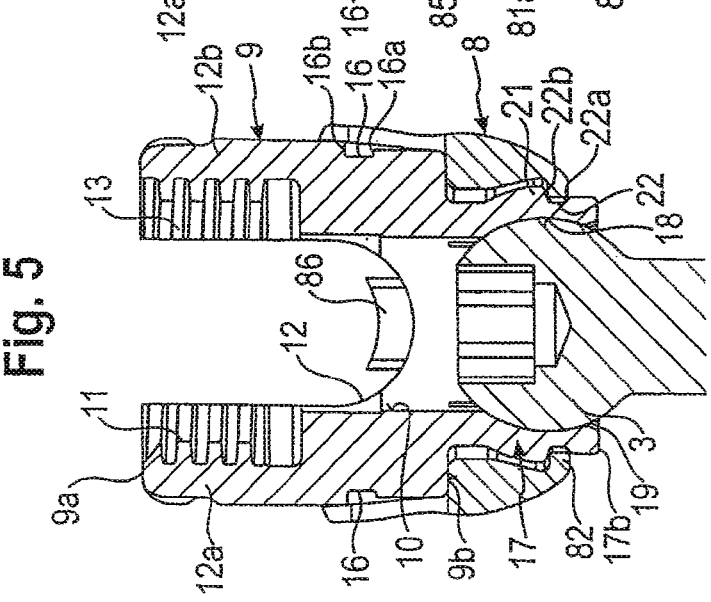
FIG. 5 shows a cross-sectional view of a bone anchoring device according to an embodiment of the invention in an assembled state, the section being taken perpendicular to a rod axis, where the locking ring is in a first position and is latched with respect to the receiving part body.
Figure 11:
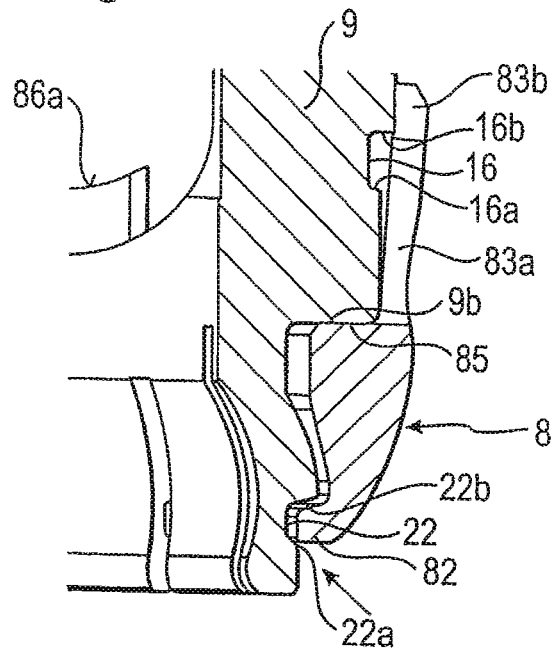
FIG. 11 shows an enlarged cross-sectional view of a portion of the receiving part, where the locking ring is in the first position and is latched with respect to the receiving part body to allow for introduction of the head.

The receiving part body 5 includes a rod receiving portion 9, which is substantially cylindrical and which has a first end 9a and a second end 9b opposite the first end 9a. A coaxial first bore 10 is provided at the second end 9b, as shown in FIGS. 5 to 7. A diameter of the first bore 10 is smaller than a diameter of the head 3 of the bone anchoring element 1. The rod receiving portion 9 further has a coaxial second bore 11 extending from the first end 9a to a distance from the second end 9b. A diameter of the second bore 11 is larger than that of the first bore 10. A substantially U-shaped recess 12 extends from the first end 9a in the direction of the second end 9b in the rod receiving portion 9, a diameter of the recess 12 being slightly larger than a diameter of the rod 6 in such a way that the rod 6 can be placed in the recess 12 and can be guided therein. By means of the recess 12, two free legs 12a, 12b are formed on which an internal thread 13 is provided. The internal thread 13 can be a metric thread, a flat thread, a negative angle thread, a saw-tooth thread, or any other type of thread. Preferably, a thread such as a flat thread or negative angle thread is used, which prevents splaying of the legs 12a, 12b when the inner screw 7 is screwed-in. The depth of the recess 12 is such that the rod 6 and the inner screw 7 can be inserted between the legs 12a and 12b.

As can be seen in FIG. 1, cut-outs 15 are provided in the rod receiving portion 9 on either end of the channel formed by the recess 12.

On an outer surface of the rod receiving portion 9, in the region of the legs 12a, 12b, a groove 16 is provided, which extends in a circumferential direction and serves for engagement with a portion of the locking ring 8. The groove 16 is asymmetric in such a way that it allows for disengagement between the locking ring 8 and the groove 16 when the locking ring 8 is shifted in one direction. The asymmetric shape of the groove 16 is realized by a downwardly inclined lower wall 16a and an upper wall 16b that is substantially perpendicular to an outer surface of the rod receiving portion 9.

At the side of the second end 9b the receiving part body 5 has a head receiving portion 17 providing an accommodation space for the head 3 of the bone anchoring element 1. A largest outer diameter of the head receiving portion 17 is smaller than a largest outer diameter of the rod receiving portion 9. An internal hollow section 18 forms a seat for the head 3 of the bone anchoring element 1, and is open via an opening 19 to a free end 17b of the head receiving portion 17. The hollow section 18 corresponds in its shape to the shape of the head 3. In the embodiment shown, the hollow section 18 is a spherical section to accommodate the spherical head 3. Furthermore, the hollow section 18 is configured to encompass the head 3 of the bone anchoring element 1 from the side, covering a region including the largest diameter of the head 3.

A plurality of slits 20 are provided in the head receiving portion 17, which are open to the free end 17b. The slits 20 make the head receiving portion 17 flexible so that it can be compressed to clamp and finally lock the head 3 in the hollow internal portion 18 by means of friction. The number and size of slits 20 is provided depending on the desired flexibility of the head receiving portion 17. The flexibility of the head receiving portion 17 is such that the head 3 of the anchoring element 1 can be inserted by expanding the head receiving portion 17, and the head 3 can be clamped by compressing the head receiving portion 17.

The outer surface of the head receiving portion 17 has a first section 21, with an outer diameter which increases towards free end 17b, for example in an outwardly curved or conically widening manner. Adjacent to the first section 21, there is a circumferential groove 22, which is recessed with respect to the first section 21 and which serves for engagement with a corresponding portion of the locking ring 8. The groove 22 is asymmetric to allow for disengagement between the locking ring 8 and the groove 22 when moving the locking ring 8 in one direction. The asymmetric shape of the groove 22 is realized by a lower downwardly inclined wall 22a and an upper wall 22b that is substantially perpendicular to an outer surface of the head receiving portion 17.

Adjacent the groove 22 on a side opposite the first section 21, there is a third portion 23 of the head receiving portion 17 with a substantially cylindrical outer surface. The third portion 23 is configured to cooperate with a portion of the locking ring 8 to enhance the clamping effect of the locking ring 8.

The locking ring 8 will now be described with reference to FIGS. 1 to 7. The locking ring 8 is substantially cylindrical and has an upper end 8a and a lower end 8b. In the mounted state the upper end 8a is oriented in the direction of the first end 9a of the rod receiving portion 9, while the lower end 8b is oriented towards the free end 17b of the head receiving portion 17. Near the lower end 8b, a first portion 81 with an inner surface 81a is provided which cooperates with the first outer surface portion 21 of the head receiving portion 17 to compress the head receiving portion 17. The outer surface of the first portion 81 may also be tapered to reduce an outer bottom diameter. The size of the first portion 81 is such that, for example, the tapered inner surface 81a can engage the outer surface portion 21 of the head receiving portion 17 to exert a compression force onto the head receiving portion 17. The inner surface 81a of the first portion 81 of the locking ring 8 can also be curved with a curvature directed towards a center of the locking ring 8.

At the lower end 8b, the locking ring 8 includes an inwardly projecting edge 82, the inner diameter of which is smaller than the inner diameter of the other portions of the locking ring 8. The inwardly projecting edge 82 is configured to engage the groove 22 of the head receiving portion 17.

The locking ring 8 further has a third portion 83 with upwardly extending wall portions 83a, which are separated from each other by slits 84. The upwardly extending wall portions 83a are arranged at an outer circumference of an inner circumferential shoulder 85 of the locking ring 8, and render the third portion 83 of the locking ring 8 flexible. The number and size of the slits 84 and the thickness of the wall portions 83a are configured such that a desired flexibility is realized. At the free ends of the wall portions 83a are engagement sections 83b which are shaped so as to engage the groove 16 provided on the outer surface of the rod receiving portion 9. The inner diameter of the third portion 83 of the locking ring 8 is only slightly larger than the outer diameter of the rod receiving portion 9, as can be seen in FIG. 5.

The locking ring 8 is sized in such a way with respect to the head receiving portion 17, that the head receiving portion 17 can expand within the locking ring 8 to allow the introduction of the head 3 when the locking ring 8 is in the first position, as shown in FIG. 5.

Two projections 86, which are located diametrically opposite to each other, are formed in the third portion 83 of the locking ring 8. The projections 86 have a height where they extend into the cut-outs 15 and project above the bottom of the substantially U-shaped recess 12 when the locking ring 8 is in a position in which the head 3 is not yet locked, as shown in FIGS. 5 and 6. A free end surface 86a of the projections 86 can be curved, particularly inwardly curved, with a curvature corresponding to an outer surface of the rod 6. The locking ring 8 is arranged in such a manner around the head receiving portion 17 of the receiving part body 5, that the projections 86 are located at the positions of (e.g., are aligned with) the recess 12. Here, the projections 86 prevent the locking ring 8 from rotating when the rod 6 is not inserted.

The flexibility of the head receiving portion 17 and the size of the head receiving portion 17 at the open end 17b allows for mounting of the locking ring 8 by assembling the locking ring 8 from the free end 17b onto the head receiving portion 17. Since the outer diameter of the head receiving portion 17 is smaller than that of the rod receiving portion 9, the locking ring 8 may only project minimally beyond the rod receiving portion 9 in a radial direction.

The inner screw 7 has a thread corresponding to the internal thread 13 provided on the legs 12a, 12b. If a thread, which prevents the legs 12a, 12b from splaying is used, a single fixation element such as the inner screw 7 is sufficient. This reduces the size of the bone anchoring device in a radial direction. Other fixation elements such as, for example, an outer nut are also possible.

The receiving part body 5, the locking ring 8, the inner screw 7 and the bone anchoring element 1 are made of biocompatible materials, for example, titanium or stainless steel or a bio-compatible alloy such as nitinol or a bio-compatible plastic material, such as polyether ether ketone (PEEK). The parts can be made of the same or of different materials.

The function of the locking ring 8 is now explained with referenced FIGS. 5 to 12. As shown in FIG. 5, the locking ring 8 is in a first position, which is an insertion position and where the locking ring 8 is latched with respect to the receiving part body 5. In the first position, the inwardly projecting edge 82 of the locking ring 8 engages groove 22 on the outer surface of the head receiving portion 17. As can be seen in the figures, the inner diameter of the inwardly projecting edge 82 is larger than the outer diameter of the head receiving portion 17 at the position of the groove 22, so as to allow for expansion of the head receiving portion 17 when the head 3 is introduced. In the first position, the locking ring 8 is additionally held by a clamping force between the rod receiving portion 9 of the receiving part body 5 and the flexible wall portions 83a of the locking ring 8, which are slightly bent outwards, as can be seen in particular in FIGS. 5, 8, and 11.

When the locking ring 8 is in the first position, the head receiving portion 17 is not compressed. In this position, the introduction of the screw head 3 is possible as can be seen in FIG. 8. In the first position, the locking ring 8 is prevented from moving upwards towards the first end 9a of the rod receiving portion 9, since the shoulder 85 of the locking ring 8 abuts against the second end 9b of the rod receiving portion 9, while the inwardly projecting edge 82 of the locking ring 8 abuts against the upper wall 22b of groove 22. As shown in particular in FIG. 8, the abutment of the locking ring 8 against the second end 9b and against the upper wall of groove 22 holds the locking ring 8 in place against upward movement. The inclined lower wall 22a of the groove 22 prevents inadvertent downward movement of the locking ring 8 but allows downward movement of the locking ring 8, upon exertion of an additional force. Since portions of the inner diameter of the locking ring 8 are larger than corresponding portions of the outer diameter of the head receiving portion 17 in a non-compressed state in the first position, an expansion of the head receiving portion 17 into a space between the locking ring 8 and the head receiving portion 17 is possible. In addition, in the first position, the head 3 can freely pivot, FIGS. 6 and 9 illustrate the bone anchoring device in a second position in which the locking ring 8 is latched with respect to the receiving part body 5 in a pre-locking position. In the second position, the locking ring 8 has been shifted from the first position towards the free end 17b of the head receiving portion 17 until the engagement portions 83b of the flexible wall portions 83a resiliently snap into the groove 16 provided on the rod receiving portion 9. Once in the second position, the free upper edge of the engagement portions 83b will abut against the upper wall 16b of the groove 16, as shown in FIGS. 6 and 9, thereby preventing upward movement of the locking ring 8 out of the pre-locking position. On the other hand, the inclined lower wall surface 16a of the groove 16 prevents inadvertent downward movement of the locking ring 8 towards the free end 17b, but allows for downward movement upon exertion of an additional force.

In the second position, as can be seen in particular in FIGS. 6 and 9, the inner inclined surface 81a of the locking ring 8 presses against the first outer surface portion 21 of the head receiving portion 17, so as to compress the head receiving portion 17 to clamp the head 3 within the hollow internal portion 18 without fully locking the head 3. In addition, the inwardly projecting edge 82 of the locking ring 8 presses against the third portion 23 of the head receiving portion 17, resulting in an additional clamping force. Therefore, clamping of the head 3 can be effected not only from above and/or the sides of the head 3, but also from a region around the lower portion of head 3. Pre-locking means that under conditions arising during surgery, the angular position of the bone anchoring element 1 with respect to the receiving part body 5 is maintained, and can be loosened only by exerting an additional force onto the receiving part body 5 and/or the bone anchoring element 1 of the bone anchoring device. In the pre-locked position, the bone anchoring element 1 cannot be removed from the receiving part 5. Hence, accidental or inadvertent removal of the head 3 is not possible. However, angulation of the bone anchoring device to be adjusted to a desired angle is still possible, for example, by manual adjustment.

Figure 12:
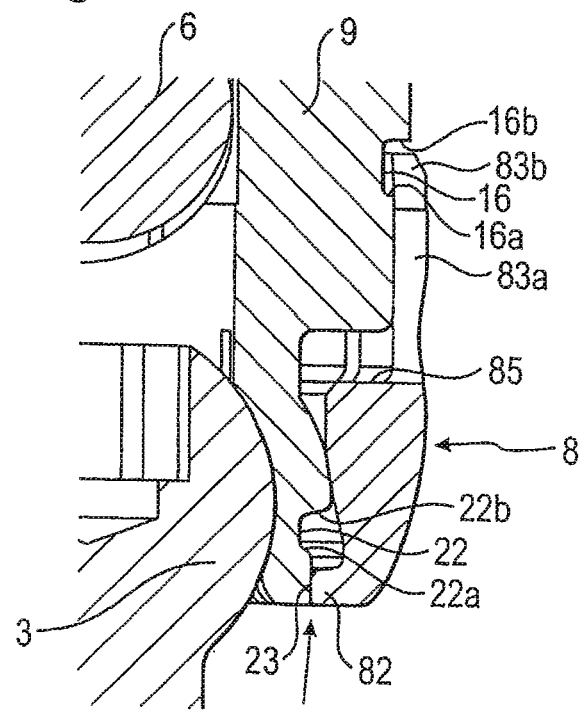
FIG. 12 shows an enlarged cross-sectional view of a portion of the bone anchoring device in a final locked state where additional clamping is effected by means of the locking ring.
Figure 15:
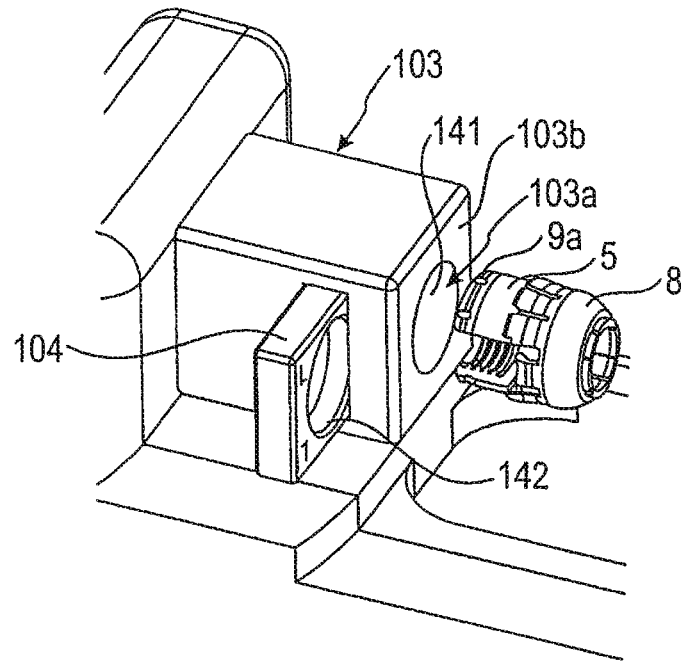
FIG. 15 shows a perspective view of a portion of the tool according to the first embodiment, with a receiving part to be inserted into a holder.
Figure 16:
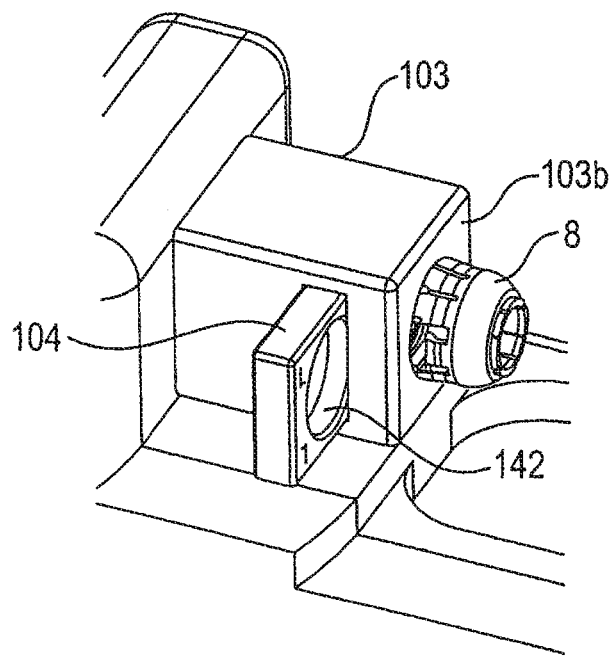
FIG. 16 shows a perspective view of a portion of the tool according to the first embodiment, with the receiving part introduced into the holder.
Figure 22:
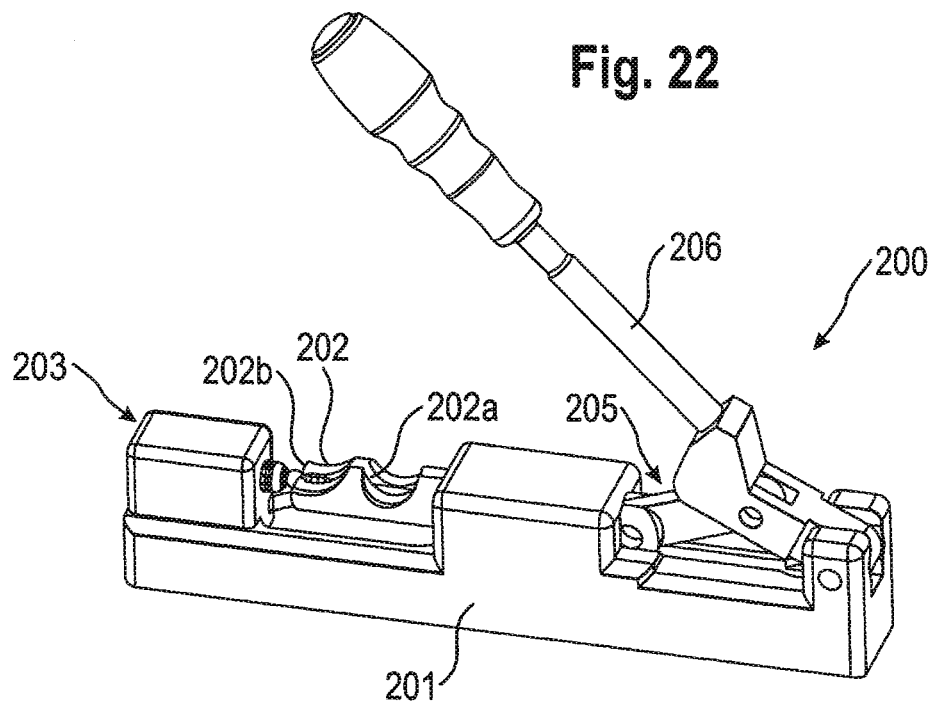
FIG. 22 shows a perspective view of a tool for assembling the bone anchoring device according to a second embodiment of the invention.

A third position, which is the locking position, is shown in FIGS. 7, 10, and 12. The third position is defined as a position in which the screw head 3 is finally locked within the head receiving portion 17. The inner surface 81a of the locking ring 8 engages the outer surface of the first portion 21 of the head receiving portion 17 in such a way that the head 3 is locked by compression of the head receiving portion 17. In addition, the inwardly projecting edge 82 of the locking ring 8 further compresses the head receiving portion 17 at the third portion 23, thereby enhancing the locking force.

The dimensions of the receiving part body 5 and the locking ring 8 are configured such that desired clamping forces can be achieved in the second position and in the third position, respectively.

The third position can be reached by shifting the locking ring 8 relative to the receiving part body 5 such that the engagement portions 83b and the inwardly projecting ring 82 slide along the lower inclined wall portions 16a and 22a of the grooves 16, 22, respectively.

The bone anchoring device is preassembled as follows. First, the locking ring 8 is mounted onto the receiving part body 5 from the free end 17*b*. This can be done, for example, by the manufacturer. Preferably, the locking ring 8 is in the first position, where it is latched by engagement or alignment of the inwardly projecting edge 82 with the groove 22.

Thereafter, the head 3 of the anchoring element 1 can be introduced from the free end 17*b* into the hollow internal portion 18 of the head receiving portion 17. Thereafter, the locking ring 8 is moved downwards relative to the receiving part body 5, so that the inwardly projecting ring 82 slides out of the groove 22 and the engagement portions 83*b* of the flexible wall portions 83*a* snap into groove 16, to reach the second position, in which the head 3 is pre-locked by frictional clamping.

A tool for assembling the bone anchoring device and its operation according to a first embodiment will now be described with reference to FIGS. 13 to 21. The tool 100 includes a frame 101 with a first holder 102 for the bone anchoring element 1 and a second holder 103 for the receiving part (including, for example, the receiving part body 5 and the locking ring 8). The holders 102, 103 are oriented such that a longitudinal axis of the bone anchoring element 1 is horizontal or parallel with respect to a surface on which the tool is placed or positioned. The first holder 102 has a recess 102*a* for the shank 2 of the bone anchoring element 1, which serves for holding and guiding the shank 2. The diameter of the recess 102*a* is smaller than the diameter of the head 3 in at least an area of a free end of the first holder 102 facing the second holder 103. Therefore, a free end surface 102*b* of the first holder 102 serves as an abutment for the head 3 of the bone anchoring element 1. The first holder 102 is supported on the frame 101.

The second holder 103 for the receiving part is also supported on the frame 101. It has a substantially circular recess 103*a* for accommodating a portion of the receiving part. The orientation of the second holder 103 with respect to the first holder 102 is such that a central axis of the receiving part is configured to be positioned coaxial with the axis of the bone anchoring element 1 when the receiving part and the bone anchoring element 1 are both inserted into their respective holders 102, 103. The circular recess 103*a* can be adjusted to have two different depths. This may be realized by an insert 104 which is inserted in a corresponding slot provided in the second holder 103 and which can be shifted in a direction transverse to the direction of the central axis of the recess 103*a*, to limit the depth of recess 103*a*. The insert 104 has one circular recess 142. In position 1, as shown in FIGS. 13 to 18, the insert limits the depth of the recess 103*a* to a first depth 141, and thus provides an abutment for the first end 9*a* of the receiving part body 5. In position 2, which is shown in FIGS. 19 to 21, the insert 104 is shifted such that its recess 142 forms or defines the bottom of the recess 103*a* of the second holder 103, the depth of which is greater than the depth 141 of the recess 103*a* when the insert 104 is in the first position. As such, the recess 142 effectively increases the length of the recess 103*a*. The receiving part can therefore be inserted deeper into the recess 103*a* until an outer surface 103*b* of the second holder 103 forms an abutment for the locking ring 8, as shown in FIGS. 19 to 21. The shape of the recess 103*a* need not be circular, but can be otherwise shaped, and in particular, it can be adapted to correspond to the contour of the receiving part.

The first holder 102 for the bone anchoring element 1 is movable relative to the second holder 103 for the receiving part body 5 in an axial direction. The first holder 102 can be actuated via a lever 105 and a handle 106. It is to be understood that the lever 105 is only an example, and that movement of the first holder 102 for the bone anchoring element 1 can be effected in many other ways, for example, by means of a toothed rack.

The dimensions of the tool 100 are configured such that, by movement of the first holder 102 for the bone anchoring element 1 with respect to the second holder 103 in which a receiving part is inserted, a sufficient force can be exerted to introduce the head 3 of the bone anchoring element 1 into the head receiving portion 17, when the recess 103*a* is set to have the first depth 141 and the locking ring 8 is in the first position. It is further configured such that a sufficient force can be exerted onto the locking ring 8 when first holder 102 is moved again relative to the second holder 103 to move the locking ring 8 out of the first position into the second position, when the recess 103*a* is set to have the second depth 142.

The operation of the tool according to the first embodiment is shown in FIGS. 17 to 21. As shown in FIGS. 17*a* and 17*b* first, the bone anchoring element 1 is inserted into the first holder 102 and the receiving part body 5, with mounted locking ring 8 in the first position, is mounted in the recess 103*a* of the second holder 103 when the recess 103*a* is set to have the first depth 141.

In a next step, as shown in FIGS. 18*a* and 18*b*, the handle 106 is actuated to actuate the lever 105 so that screw head 3 is pushed into the hollow internal portion 18 of the head receiving portion 17. The bottom of the recess 103*a* of the second holder 103 serves as an abutment for the receiving part, so that the head receiving portion 17 can expand to allow the introduction of the head 3. The handle 106 is actuated until the head 3 of the bone anchoring element 1 is latched or inserted in the hollow internal portion 18. The latching may produce an audible sound.

Thereafter, as shown in FIGS. 19 to 21, the first holder 102 for the bone anchoring element 1 is shifted backward and the insert 104 is moved to the second position, in which the circular recess 142 forms or defines the bottom of recess 103*a* to provide and use outer surface 103*b* of holder 103 as an abutment for the locking ring 8.

As shown in FIGS. 20 and 21, the handle 106 is then actuated to push the first holder 102 towards the second holder 103. By means of this, the head 3 with the receiving part body 5 is pushed farther into the bottom of the recess 103*a*, which has a depth where the free front surface 103*b* of the second holder 103 presses against the engagement portions 83*b* of the flexible wall portions 83*a* of the locking ring 8, thereby moving the locking ring 8 out of the first position into the second position, where the engagement portions 83*b* are latched in the groove 16 on the rod receiving portion 9. When the engagement portions 83*b* snap into the groove 16, the latching of the locking ring 8 with respect to the receiving part body 5 may be audible, which indicates that the correct pre-locking position is reached.

Thereafter, the first holder 102 is moved backward and the bone anchoring device is removed.

A tool for assembling the bone anchoring device and its operation according to a second embodiment will now be described with reference to FIGS. 22 to 28*c*. As can be seen from FIG. 22, the tool 200 includes a frame 201 with a first holder 202 for the bone anchoring element 1 and a second holder 203 for the receiving part (again including, for example, the receiving part body 5 and the locking ring 8). The tool 200 according to the second embodiment only differs from the tool 100 according to the first embodiment in that the second holder 203 is different from the second holder 103 according to the first embodiment. The holders 202, 203 may be oriented such that a longitudinal axis of the bone anchoring element 1 is horizontal or parallel with respect to a surface on which the tool is placed or positioned. The holder 202 has a recess 202a for the shank 2 of the bone anchoring element 1, which serves for holding and guiding the shank 2. The diameter of the recess 202a is smaller than the diameter of the head 3 in at least an area of a free end of the first holder 202 facing the second holder 203. Therefore, a free end surface 202b of the first holder 202 serves as an abutment for the head 3 of the bone anchoring element 1. The first holder 202 is supported on the frame 201.

The second holder 203 for the receiving part is also supported on the frame 201. The orientation of the second holder 203 with respect to the first holder 202 is such that a central axis of the receiving part is configured to be positioned coaxial with the axis of the bone anchoring element 1 when the receiving part and the bone anchoring element 1 are both inserted into their respective holders 202, 203.

The first holder 202 for the bone anchoring element 1 is movable relative to the second holder 203 for the receiving part body 5 in an axial direction. The first holder 202 can be actuated via a lever 205 and a handle 206. It is to be understood that the lever 205 is only an example, and that movement of the first holder 202 for the bone anchoring element 1 can be effected in many other ways, for example, by means of a toothed rack.

Figure 23:
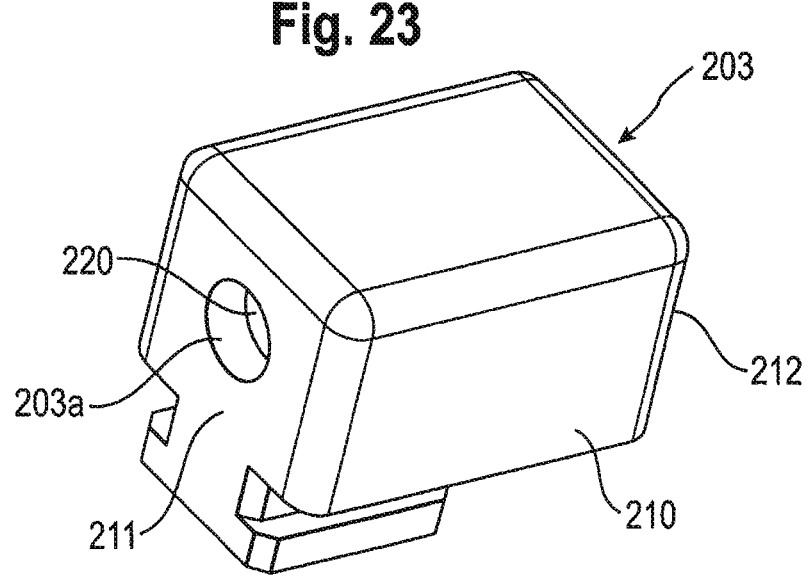
FIG. 23 shows a perspective view of a second holder according to the second embodiment.
Figure 24:
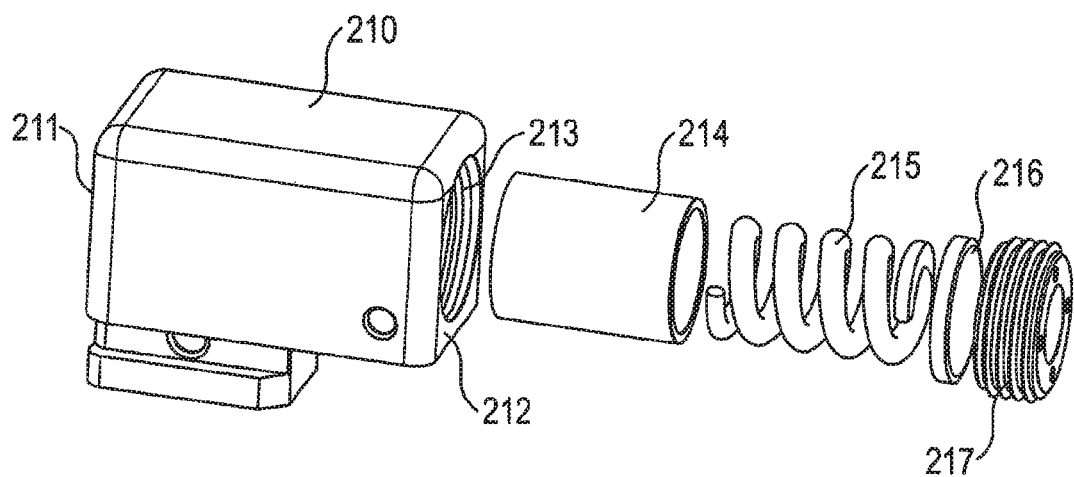
FIG. 24 shows a perspective exploded view of the second holder according to the second embodiment.

As can be seen from FIG. 23, the second holder 203 includes a main body 210, a first end 211, a second end 212, a bore 220, and a substantially circular recess 203a for accommodating a portion of the receiving part. As can be seen from FIG. 24 the second holder 203 further includes a thread 213, a sleeve 214, a spring 215, a plate 216 and a screw 217. As can be seen from FIGS. 25a and 25b, the cup-shaped sleeve 214 is closed on a side extending towards the first end 211 and is configured to slide within the bore 220 of the main body 210 since its diameter is slightly smaller than the inner diameter of at least a portion of the bore 220. The spring 215 is provided within the sleeve 214 and is supported by the plate 216 and the inner screw 217 which is screwed into the thread 213 of the main body 210. Other designs for supporting the spring 215 are possible, such as for example, a base which is press-fitted into the second holder 203. The spring 215 is shown as a helical spring 215 in the second embodiment. However other spring elements are possible, such as leaf springs, disk springs, elastomer cushions, etc.

Figure 25A:
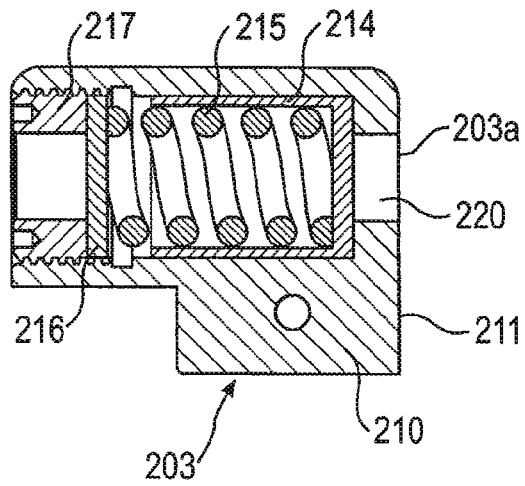
FIG. 25a shows a cross-sectional view of the second holder in a first position according to the second embodiment.
Figure 25B:
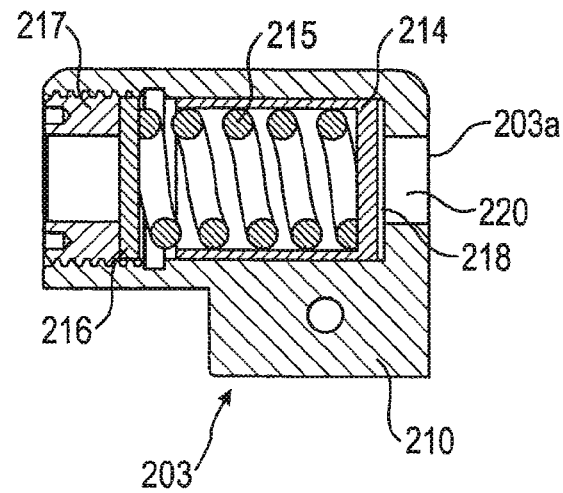
FIG. 25b shows a cross-sectional view of the second holder in a second position according to the second embodiment.

The circular recess 203a can have varying depths. This is realized by the movable sleeve 214 which provides an abutment for the receiving part. In FIG. 25a a first abutment position and in FIG. 25b a second abutment position are shown, where a space 218 is shown in FIG. 25b when the spring 215 is compressed. The sleeve 214 provides an abutment for the first end 9a (see FIG. 1) of the receiving part body 5. In the first abutment position, the closed side of the sleeve 214 forms the bottom of the recess 203a of the second holder 203, the depth of which is less than a depth of the recess 203a in the second abutment position that is achieved when a greater force is applied by the first end 9a of the receiving part onto the sleeve 214 and the spring 215, respectively. The force is exerted by the handle 206 and the lever 205 via the first holder 202, the shaft 2 and the head 3 to the first end 9a of the receiving part and then to the sleeve 214. The shape of the recess 203a need not be circular, but can be otherwise shaped, and in particular, it can be adapted to correspond to any possible contour of the receiving part.

The dimensions of the tool 200 and the spring force are configured such that, by means of moving the first holder 202 with the bone anchoring element 1 relative to the second holder 203 in which a receiving part is inserted, a first force can be exerted to introduce the head 3 of the bone anchoring element 1 into the head receiving portion 17, when the recess 203a is set to have the first depth and the locking ring 8 is in the first position. It is further configured such that a second force can be exerted onto the locking ring 8 when the first holder 202 is moved closer relative to the second holder 203 to move the locking ring 8 out of the first position into the second position, where the recess 203a has the second depth. The tool 200 according to the second embodiment of the invention allows for mounting of various bone anchoring devices with, for example, receiving parts having different heights and/or various different locking ring positions relative to the receiving part.

Figure 27:
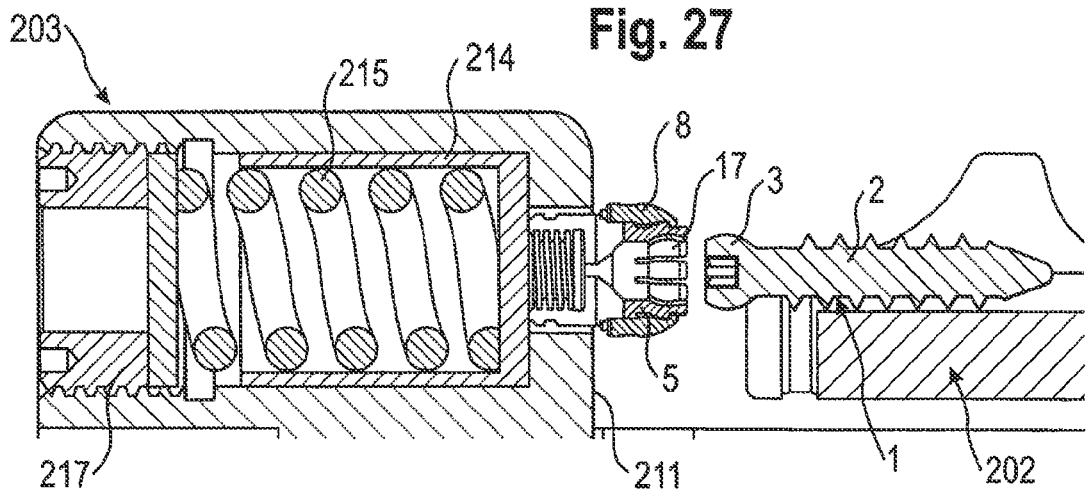
FIG. 27 shows a cross-sectional view of a portion of the tool according to the second embodiment in the first position of use.

The operation of the tool according to the second embodiment is shown in FIGS. 26a to 28c. As shown in FIGS. 26a, 27 and 28a first, the bone anchoring element 1 is inserted into the first holder 202 and the receiving part body 5, with mounted locking ring 8 in the first position, is mounted in the recess 203a of the second holder 203 when the recess is set to have the first depth.

Figure 28A:
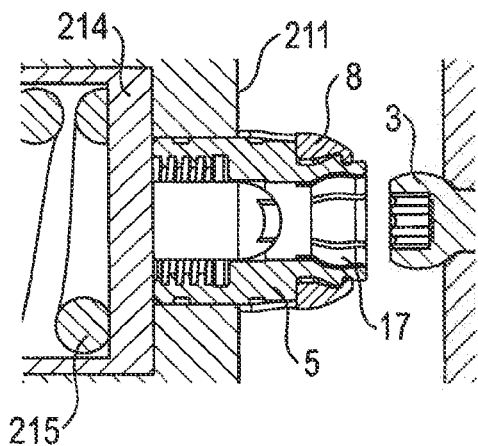
FIG. 28a shows a cross-sectional view of an enlarged portion of the tool in the first position of use according to the second embodiment.
Figure 28B:
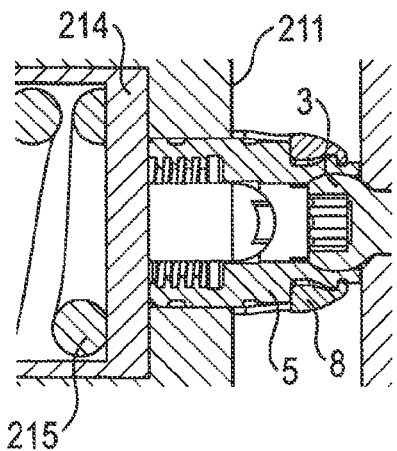
FIG. 28b shows a cross-sectional view of an enlarged portion of the tool in the second position of use according to the second embodiment.

In a next step, as shown in FIGS. 26b and 28b, the handle 206 is actuated to actuate the lever 205 (see FIG. 22) so that the screw head 3 is pushed into the hollow internal portion 18 (see FIG. 5) of the head receiving portion 17. The bottom of the recess 203a of the second holder 203, i.e. the sleeve 214, serves as an abutment for the receiving part, so that the head receiving portion 17 can expand to allow the introduction of the head 3. The handle 206 is actuated until the head 3 of the bone anchoring element 1 is latched or inserted in the hollow internal portion 18. The latching may produce an audible sound. The locking ring 8 may not yet contact a side wall of the first end 211. The counterforce of the spring 215 is greater than the counterforce from insertion of the head 3 into the receiving part body 5. Therefore, the spring 215 is not compressed during this step.

Figure 28C:
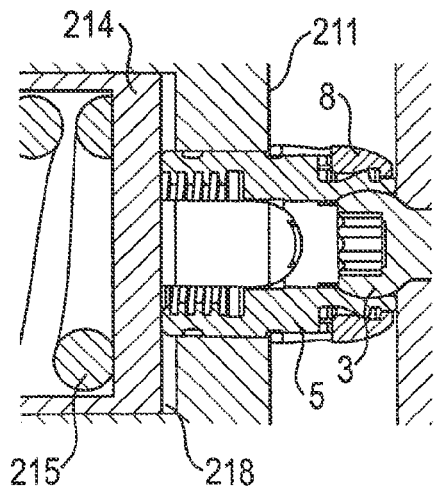
FIG. 28c shows a cross-sectional view of an enlarged portion of the tool in the third position of use according to the second embodiment.

As shown in FIGS. 26c and 28c, the handle 206 is then actuated further to push the first holder 202 closer to the second holder 203. By means of this, the head 3 with the receiving part body 5 is pushed against the bottom of the recess 203a, i.e. the sleeve 214. The force which is needed for moving the locking ring 8 and the receiving part body 5 relative to each other is greater than the counterforce from the spring 215. Therefore, the spring 215 is compressed. The recess 203a now has a depth where the side wall of the first end 211 of the second holder 203 presses against the engagement portions 83b of the flexible wall portions 83a of the locking ring 8 (see FIG. 3), thereby moving the locking ring 8 out of the first position into the second position, where the engagement portions 83b are latched in the groove 16 on the rod receiving portion 9. When the engagement portions 83b snap into the groove 16, the latching of the locking ring 8 with respect to the receiving part body 5 may be audible, which may indicate that the correct pre-locking position is reached.

Thereafter, the first holder 202 is moved backward and the bone anchoring device is removed. One advantage of the second embodiment of the tool 200 as compared to the first embodiment of the tool 100 is that only a singe actuation of the handle 206 is needed, and no additional parts have to be moved during the mounting of the bone anchoring device.

By means of the tool 200 according to the second embodiment, assembly of the bone anchoring device can be easily completed in one step, including the introduction of the head and the mounting of the bone anchoring device into the pre-lock position.

A third embodiment of a first holder 302 for the bone anchoring element will now be described with reference to FIGS. 29 to 33. The tool 300 shown in FIG. 29 can be the same as the tool 100 or 200 described above, or have similar features, except for the first holder 302, which replaces the first holders in the previous embodiments.

Figure 31:
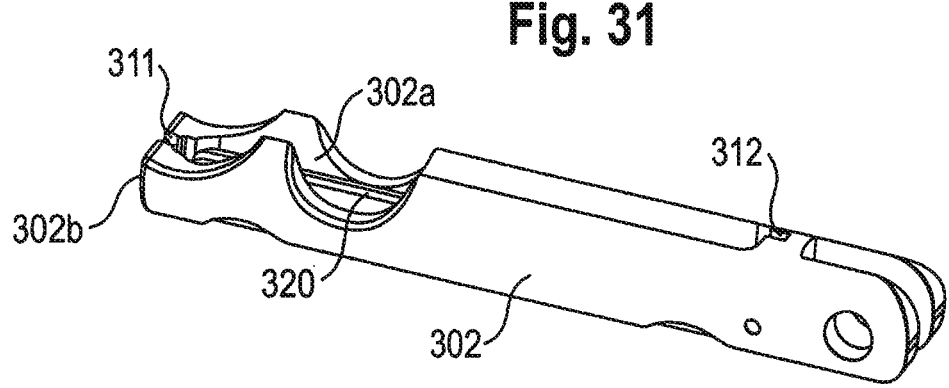
FIG. 31 shows the first holder and the insert in an assembled state according to the third embodiment.

The first holder 302, shown in FIGS. 30*b* and 31, has a longitudinal U-shaped recess 302*a* which referring to FIG. 30*b*, extends from one end towards another end in a longitudinal direction and from the side of the first holder 302 inwards. The diameter of the recess 302*a* is smaller than the diameter of a head 3 of a bone anchoring element 1. Therefore, a free end surface 302*b* of the first holder 302 serves as an abutment for the head 3 of the bone anchoring element 1. The first holder 302 is supported on the frame 301.

Figure 32:
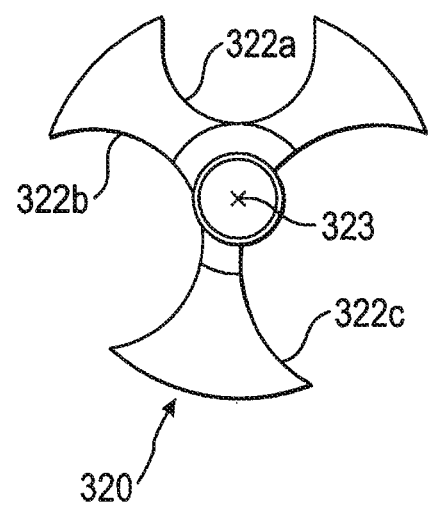
FIG. 32 shows a cross-sectional view of the insert according to the third embodiment.

FIG. 30*a* and FIG. 32 show an insert 320 according to a third embodiment for the first holder in the form of a cylindrical section having a plurality of longitudinally extending recesses 322*a*, 322*b*, 322*c* that are arranged circumferentially around a central axis 323 of the insert 320. The recesses are sized and/or adapted for the insertion of screws or other bone anchoring elements with different shanks. h the embodiment shown the insert 320 has a first cylinder-shaped or U-shaped recess 322*a* having a first radius, a second cylinder-shaped or U-shaped recess 322*b* having a second radius, and a third cylinder-shaped or U-shaped recess 322*c* having a third radius, where the three radii may be different from each other. The three recesses 322*a*, 322*b*, 322*c* may extend the length of the insert 320, as can be seen from FIG. 30*a*. The insert 320 has a first end and a second end, wherein a first pin 321*a* is provided on the first end and a second pin 321*b* is provided on the second end. The pins 321*a*, 321*b* are in line with the central axis 323 of the insert 320.

Referring to FIG. 30*b*, the first holder 302 has a first end and a second end, where on the first end a first slot 311 is provided and near the second end a second slot 312 is provided which both extend from a side of the first holder 302 inwards. The second end of the first holder 302 is configured to be connected to a lever 305 and a handle 306 of the tool 300, as can be seen in FIG. 29.

The U-shaped recess 302*a* of the first holder 302 is provided for receiving the insert 320. The radius of the circular portion of the U-shaped recess 302*a* may be substantially the same as the radius of the insert 320.

Figure 33:
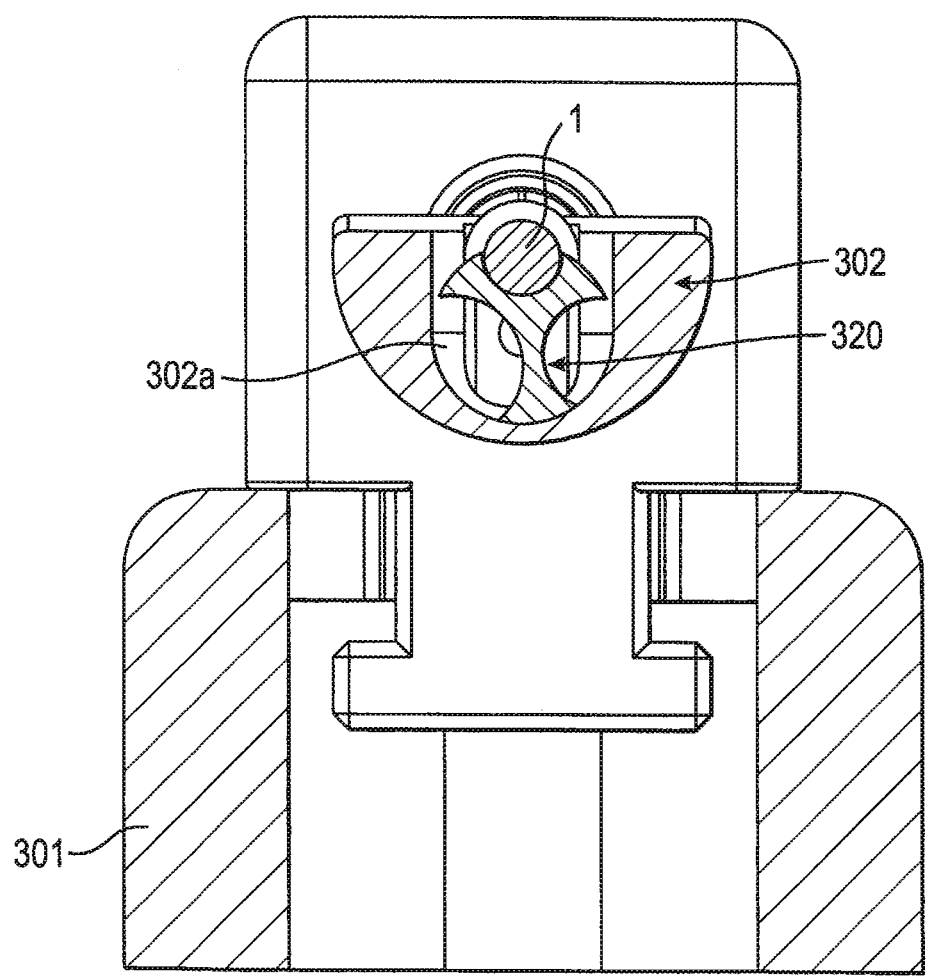
FIG. 33 shows a cross-sectional view of a frame, the first holder, and the insert, the assembly holding a screw according to the third embodiment.

As can be seen from FIG. 31, in a mounted state, the first pin 321*a* of the insert 320 fits into the first slot 311 of the first holder 302, and the second pin 321*b* of the insert 320 fits into the second slot 312 of the first holder 302. The insert 320 is supported and guided by the pins 321*a*, 321*b*, and is also held by the U-shaped recess 302*a* of the first holder 302, as can be seen in FIG. 33.

The orientation of the first holder 302 with respect to a second holder (e.g., second holder 103 or 203 as seen in the previous tool embodiments) is such that a central axis of a receiving part 5 is configured to be positioned coaxial with an axis of the bone anchoring element 1 when the receiving part 5 is inserted into the second holder and the bone anchoring element 1 is inserted into the first holder 302 in one of the recesses 322*a*, 322*b* or 322*c* of the insert 320.

The three recesses 322*a*, 322*b* or 322*c* are adapted to receive different sized shanks of bone anchoring elements. With reference to FIGS. 29, 31, and 33, a particular recess 322*a*, 322*b*, 322*e* which is in use will face outwards towards the opening of the U-shaped recess 302*a*. In this embodiment of the insert 320, mounting of at least three different sized bone anchoring elements can be accommodated. For changing the recess 322*a*, 322*b*, 322*c* which is in use, the insert 320 can be rotated around its axis 323.

A fourth embodiment of a first holder 402 for the bone anchoring element 1 will now be described with reference to FIGS. 34 to 47. The tool 400 shown in FIG. 34 can be the same tool 200 or 300 described above, or have similar features, except for the first holder 402 which replaces the first holders in the previous embodiments.

Figure 36:
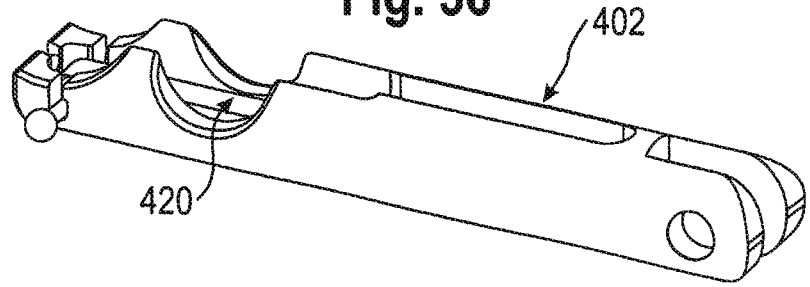
FIG. 36 shows a perspective view of the insert and the first holder according to the fourth embodiment in an assembled state.

The first holder 402, shown in FIGS. 34 to 41, has a longitudinal U-shaped recess 402*a* which referring to, for example, FIG. 36, extends from one end towards another end in a longitudinal direction and from the side of the first holder 402 inwards. The diameter of the recess 402*a* is smaller than the diameter of the head 3 of the bone anchoring element 1 at at least an end of the first holder 402. Therefore, a free end surface 402*b* of the first holder 402 serves as an abutment for a head 3 of a bone anchoring element 1 by means of a semicircular recess. The first holder 402 is supported on the frame 401. Furthermore, adjacent to the free end surface 402*b*, a slot 423 perpendicular or transverse to the U-shaped recess 402*a* is provided that extends into the recess 402*a*. Referring to the illustration in FIG. 37, the slot 423 intersects an upper region of the two legs of the U-shaped recess 402*a*.

FIGS. 35 and 42 to 45 show an insert 420 for the first holder 402 according to the fourth embodiment, in the form of a cylindrical section having a first longitudinally extending recess 422*a* and a second longitudinally extending recess 422*b* that are arranged on opposite sides of the insert 420. The recesses 422*a* and 422*b* are sized and/or adapted for insertion of screws or other bone anchoring elements 1 with different shanks. In the embodiment shown, the first cylinder-shaped or U-shaped recess 422*a* has a first radius, for example, for receiving 4-6 mm shanks, and the second cylinder-shaped or U-shaped recess 422*b* has a second radius, for example for receiving 7-9 mm shanks. Other radii combinations for the two recesses 422*a* and 422*b* are also possible. The recesses 422*a* and 422*b* may extend the full length of the insert 420, as can be seen from FIGS. 35, 42-44.

The insert 420 has a first end and a second end, wherein a pin 424 is provided on the first end that extends perpendicular or transverse to the longitudinal recesses 422*a* and 422*b*. As can be seen from FIG. 42, the pin 424 has a spherical end portion and is provided on the cylindrical outer wall of the insert 420.

Figure 34:
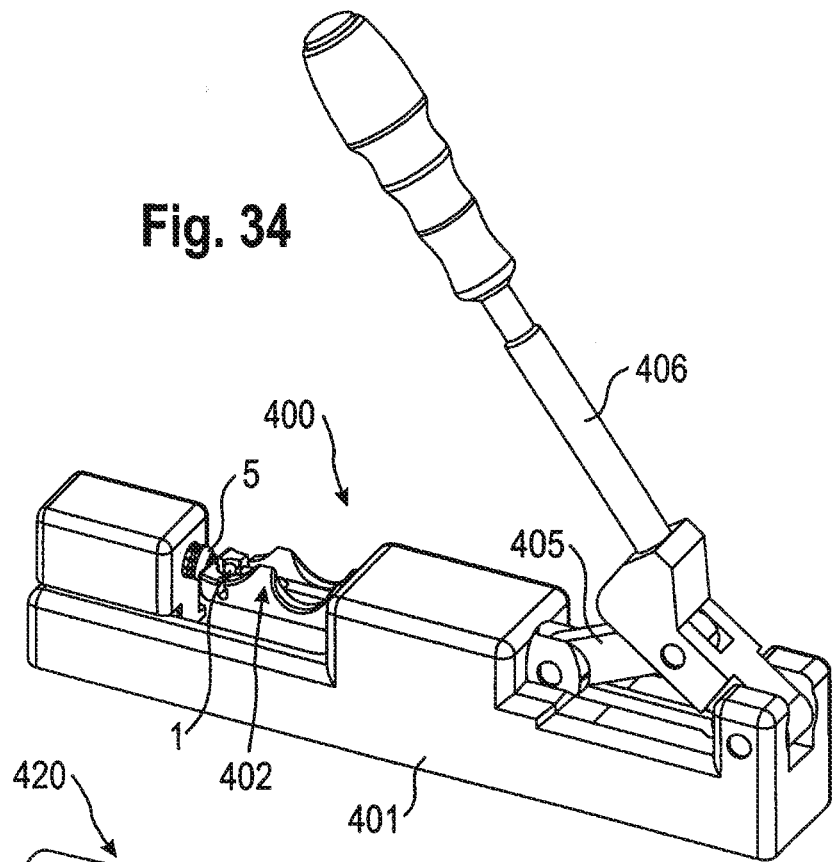
FIG. 34 shows a perspective view of a tool according to a fourth embodiment of the invention, depicting a step of assembly where a head of a bone anchoring element is to be inserted into a receiving part.
Figure 35:
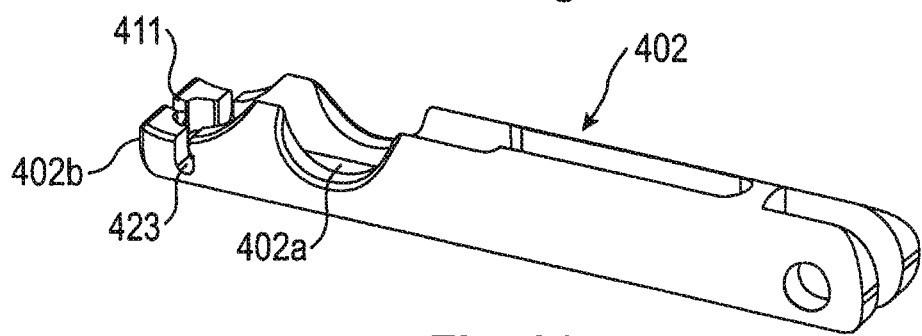
FIG. 35 shows a perspective view of an insert and a first holder according to the fourth embodiment prior to assembly.
Figure 37:
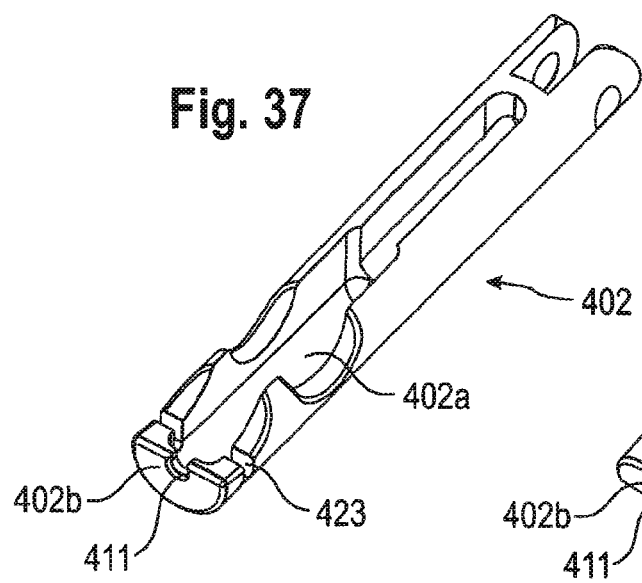
FIG. 37 shows a perspective top view of the first holder according to the fourth embodiment.
Figure 38:
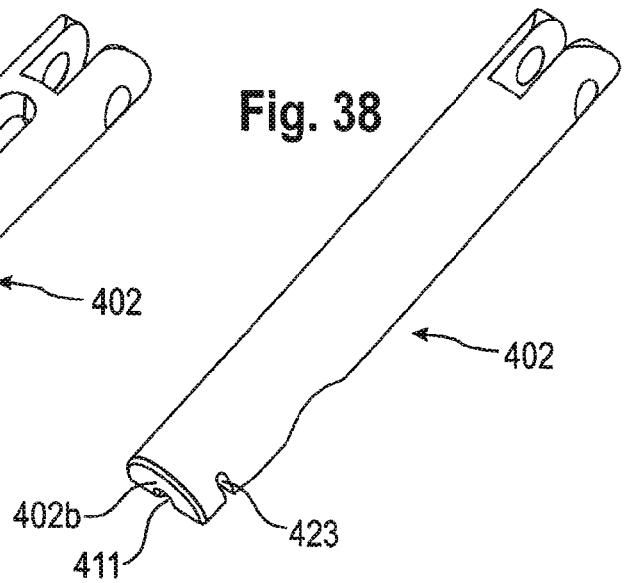
FIG. 38 shows a perspective bottom view of the first holder according to the fourth embodiment.
Figure 39:
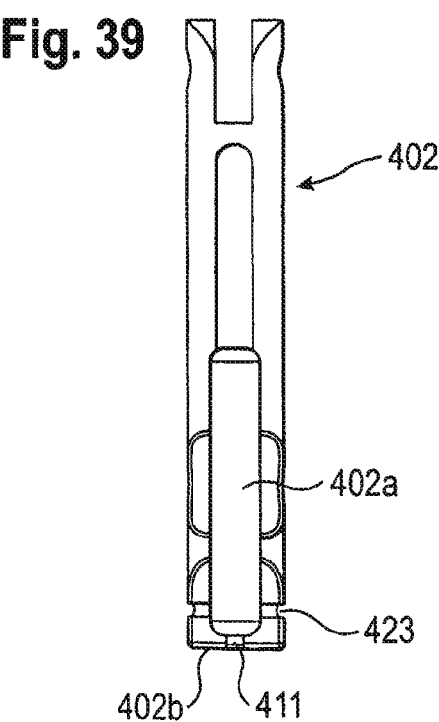
FIG. 39 shows a top view of the first holder according to the fourth embodiment.
Figure 40:
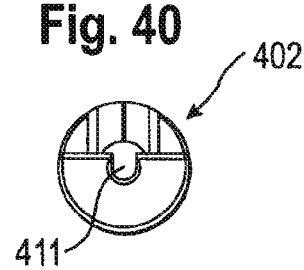
FIG. 40 shows a side view of the first holder according to the fourth embodiment.
Figure 41:
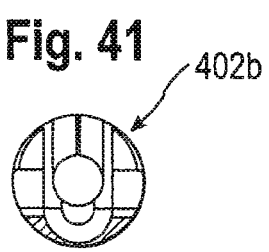
FIG. 41 shows another side view of the first holder according to the fourth embodiment.
Figure 42:
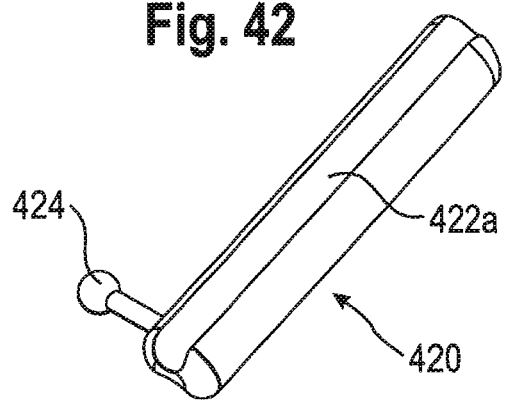
FIG. 42 shows a perspective view of the insert according to the fourth embodiment in a first position.
Figure 43:
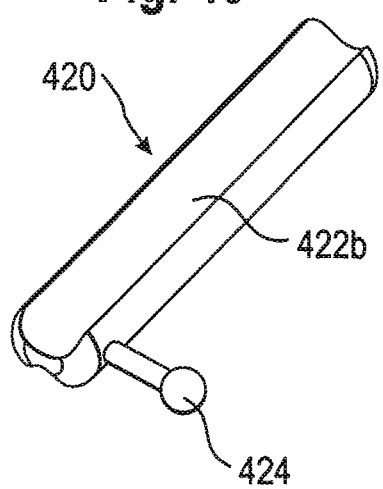
FIG. 43 shows a perspective view of the insert according to the fourth embodiment in a second position.
Figure 44:
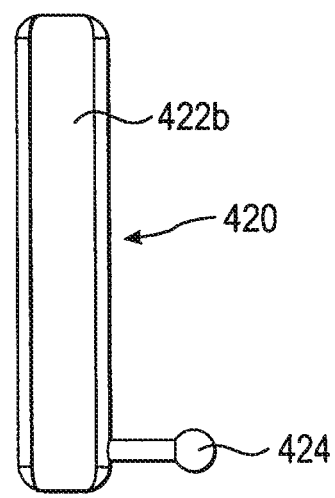
FIG. 44 shows a top view of the insert according to the fourth embodiment.
Figure 45:
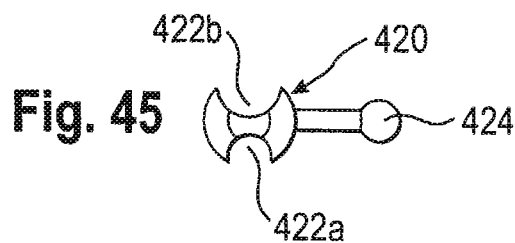
FIG. 45 shows a side view of the insert according to the fourth embodiment.

Referring to FIG. 37, the first holder 402 has a first end and a second end, wherein on the first end a slot 411 is provided which extends from a side of the first holder 402 inwards. The second end of the first holder 402 is configured to be connected to a lever 405 and a handle 406 of the tool 400, as can be seen in FIG. 34.

Figure 46:
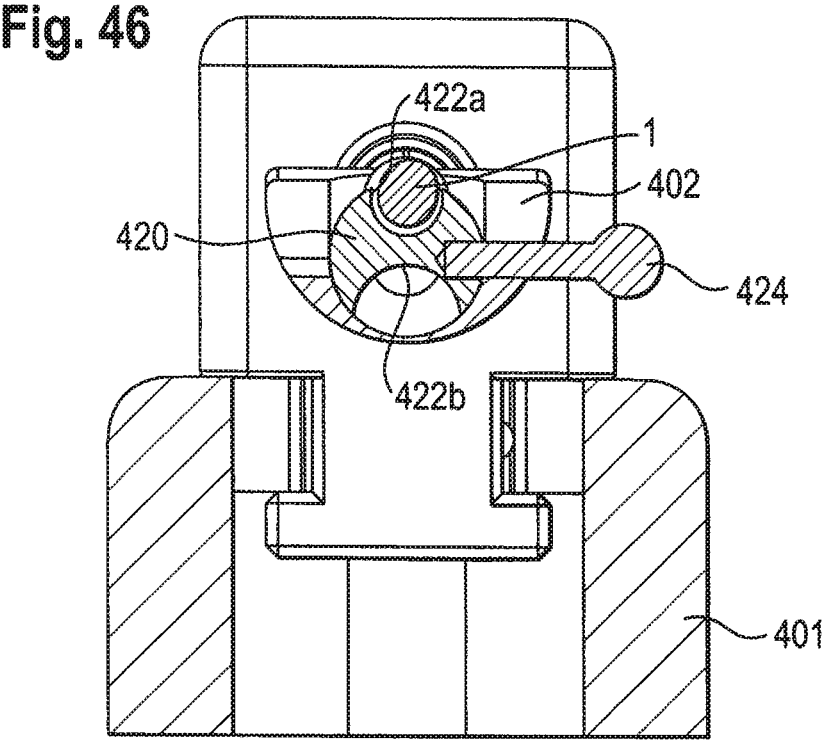
FIG. 46 shows a cross-sectional view of a frame, the first holder, and the insert in a first position, the assembly holding a screw according to the fourth embodiment.
Figure 47:
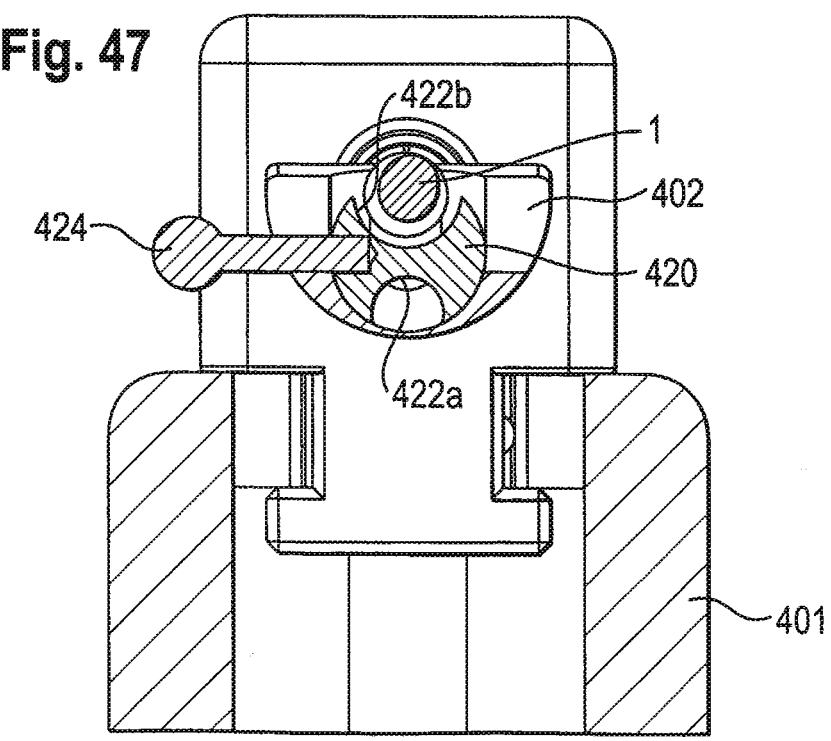
FIG. 47 shows a cross-sectional view of the frame, the first holder, and the insert in a second position, the assembly holding a screw according to the fourth embodiment.

The U-shaped recess 402*a* of the first holder 402 is provided for receiving the insert 420 (see FIG. 36). A radius of the circular portion of the U-shaped recess 402*a* may be substantially the same as an outer radius of the insert 420. As can be seen from FIG. 36, in a mounted state, the pin 424 of the insert 420 fits into the slot 423 of the first holder 402, where the pin 424 may be received by the slot 423 in two positions by rotating the insert 420, for example, by using the pin 424. The insert 420 is supported and guided by the U-shaped recess 402*a* of the first holder 402, as can be seen in FIGS. 46 and 47.

An orientation of the first holder 402 with respect to the second holder, such as second holder 103 or 203, is such that a central axis of a receiving part 5 is configured to be positioned coaxial with an axis of a bone anchoring element 1 when the receiving part 5 is inserted into the second holder and the bone anchoring element 1 is inserted into the first holder 402 in one of the recesses 422*a* or 422*b* of the insert 420.

The recesses 422*a* or 422*b* are adapted to receive different sized shanks of bone anchoring elements. With reference to FIGS. 34, 36, 46, 47, a particular recess 422a, 422b which is in use will face outwards or upwards towards the opening of the U-shaped recess 402a. In this embodiment of the insert 420, mounting of at least two different sized bone anchoring elements 1 can be accommodated, For changing the recess 422a, 422b which is in use, the insert 420 can be rotated around its axis by means of the pin 424. By utilizing the pin 424 and the corresponding slot 423, two positions of the insert 420 are defined based on the position of the pin 424 in one of the two legs of the U-shaped recess 402a. By providing only two recesses 422a and 422b, the insert 420 is easy to clean and sterilize. Providing a pin similar to the pin 424 for rotating the insert 320 in the third embodiment is also possible. In that case, three defined positions of the pin would be provided, for example, by means of two short slots and a hole in the ground or bottom of the longitudinal recess 302a.

In other embodiments, a cylinder or insert having one or more than three recesses can be provided. With the embodiments of the holder, a user can combine screws or bone anchoring elements with different shanks to a receiving part. Hence, a modular system is provided that gives the user a wider selection of implant combinations depending on the actual clinical situation.

The bone anchoring device can be preassembled either by the manufacturer or in the course of preparation of surgery or at any other time. Advantageously, the surgeon can select prior to surgery the desired receiving parts and bone anchoring elements according to the specific requirements of the particular clinical application. The design of the bone anchoring device allows for selection of the appropriate bone anchoring elements in terms of diameter, length and other features of the anchoring section. Hence, a modular system can be provided, which includes receiving parts and various bone anchoring elements, which then can be individually chosen and adapted.

In use, during surgery, a preassembled bone anchoring device including the receiving part body 5, the bone anchoring element 1, and the locking ring 8 in the pre-locking position, is screwed into a bone. The recess 4 of the head 3 can be accessed with a screw tool through the first bore 10. To correctly align the receiving part body 5 with respect to the rod 6, to which it will be connected, an additional force can be exerted onto the receiving part, either manually or by application of an instrument. Once the correct position of the rod 6 with respect to other bone anchoring devices is also achieved, the inner screw 7 can be tightened for each bone anchoring device. Since the rod 6 abuts against the projections 86 of the locking ring 8, the locking ring 8 is shifted downward into the third position, which is the locking position. When the locking ring 8 is moved towards the free end 17b of the head receiving portion 17, it compresses the head receiving portion 17, thereby locking a position of the head 3. Final tightening of the inner screw 7 locks the rod 6 and the head 3 simultaneously.

In the pre-locking condition, the head 3 remains clamped when the inner screw 7 is loosened. This allows further adjustments with respect to positioning of the rod 6.

Further modifications to bone anchoring devices which are compatible with tools according to the embodiments shown are possible. For example, the head of the bone anchoring element can have any other shape, for example, a cylindrical shape, whereby a monoaxial bone screw is provided, allowing rotation of the screw element with respect to the receiving part body around a single axis. The head can also be conically shaped or otherwise shaped, and the internal hollow section of the head receiving portion is adapted to correspond to this shape. In a further modification, the flexibility of the head receiving portion is based on properties of the material, for example, a plastic material, and the slits may be fully or partly omitted.

The projections of the locking ring which engage the rod can have another shape, for example, the surface of the free end can be flat or can be otherwise shaped. Alternatively, the projections can be omitted.

The head receiving portion can have an inclined open end, or can be otherwise asymmetric to allow for a greater angulation of the head in one direction.

The outer surface of the head receiving portion and the inner surface of the locking ring can have other shapes which allow for compression of the locking ring by means of an increasing force when the locking ring is shifted downwards relative to the receiving part body.

With respect to the tools, variations are also possible. For example, the tool can be configured such that the screw axis and the central axis of the receiving part extend perpendicular to the surface on which the tool is placed or positioned. The second holder for the receiving part body can be movable with respect to the first holder for the bone anchoring element, hi addition, instead of a manual actuation of the tool, it may also be possible to actuate the tool by means of a mechanically or electronically operated device.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A tool for assembling a bone anchoring device, the bone anchoring device comprising a bone anchoring element with a head and a shaft to be anchored in bone and a receiving part, the tool comprising:
a first holder for the bone anchoring element having an insert configured to be inserted into a longitudinal recess of the first holder, wherein the insert is capable of receiving the bone anchoring element, wherein at least two recesses configured to receive different sized bone anchoring elements are formed at an outer surface of the insert, and wherein respective longitudinal axes of the recesses of the insert are spaced apart from one another.

2. The tool according to claim 1, wherein the insert is rotatable in the first holder.

3. The tool according to claim 1, wherein the insert has a pin.

4. The tool according to claim 3, wherein the insert is rotatable in the first holder via the pin.

5. The tool according to claim 3, wherein the pin is provided on one end of the insert and extends perpendicular to the at least two recesses of the insert.

6. The tool according to claim 3, wherein the pin fits into a slot of the first holder that extends perpendicular to the longitudinal recess of the first holder.

7. The tool according to claim 1, wherein the respective longitudinal axes of the at least two recesses of the insert are parallel to one another.

8. The tool according to claim 1, wherein the recesses of the insert are cylinder-shaped or U-shaped.

9. The tool according to claim 1, wherein the recesses of the insert each extends over a whole length of the insert.

10. The tool according to claim 1, wherein the insert is substantially cylindrical.

11. The tool according to claim 1, wherein two of the recesses of the insert are positioned circumferentially on opposite sides of the insert.

12. An insert for a tool for assembling a bone anchoring device comprising a bone anchoring element with a head and a shaft to be anchored in bone and a receiving part, the insert configured for insertion into a holder of the tool, the insert comprising an elongate body with a longitudinal axis;
wherein a first recess configured to receive a shaft of a bone anchoring element extends on a surface of the elongate body along the longitudinal axis, has a first diameter, and is oriented towards a first radial direction relative to the longitudinal axis;
wherein a second recess configured to receive a shaft of a bone anchoring element extends on a surface of the elongate body along the longitudinal axis, has a second diameter greater than the first diameter, and is oriented towards a second radial direction relative to the longitudinal axis different than the first radial direction.

13. The insert according to claim 12, wherein the recesses are cylinder-shaped or U-shaped.

14. The insert according to claim 12, wherein the recesses each extend over a whole length of the insert.

15. The insert according to claim 12, wherein the body of the insert is substantially cylindrical.

16. The insert according to claim 12, wherein the first and second recesses are positioned on opposite sides of the insert.

17. A tool for assembling a bone anchoring device, the bone anchoring device comprising a bone anchoring element with a head and a shaft to be anchored in a bone and a receiving part, the tool comprising:
a first holder configured to hold a bone anchoring element;
a second holder configured to hold a receiving part; and
an insert configured to be positioned in the first holder, the insert having an elongate body with a longitudinal axis, and having a first recess and a second recess each configured to receive a shaft of a bone anchoring element, wherein the first and second recesses each extend on a surface of the elongate body along the longitudinal axis, have different diameters, and are oriented in different radial directions relative to the longitudinal axis.

18. The tool according to claim 17, further comprising a pin on the insert.

19. The tool according to claim 18, wherein the insert is rotatable via the pin when the insert is positioned in the first holder of the tool.

20. The tool according to claim 18, wherein the pin is provided on one end of the insert and extends perpendicular to the longitudinal axis.

21. The tool according to claim 18, wherein the pin is configured to fit into a slot of the first holder of the tool.

22. The tool according to claim 21, wherein the first holder has a recess for holding the insert, the slot extends perpendicular to the recess of the first holder, and the pin of the insert is configured to fit into the slot.

23. The tool according to claim 17, wherein the insert is substantially cylindrical.

24. The tool according to claim 17, wherein the insert is rotatable in the first holder.

25. The tool according to claim 17, wherein the first and second recesses are positioned on opposite sides of the insert.

26. The tool according to claim 17, wherein the first holder and the second holder are configured to move relative one another to assemble a bone anchoring element that is held by the first holder with a receiving part that is held by the second holder.

27. The tool according to claim 17, wherein the insert is configured for insertion into and removal from the first holder of the tool.

28. A method for assembling a bone anchoring device with a tool, the bone anchoring device comprising a bone anchoring element with a head and a shaft to be anchored in a bone and a receiving part, the tool comprising a first holder configured to hold a bone anchoring element, a second holder configured to hold a receiving part, and an insert configured to be positioned in the first holder, the insert having an elongate body with a longitudinal axis, and having a first recess and a second recess each configured to receive a shaft of a bone anchoring element, wherein the first and second recesses each extend on a surface of the elongate body along the longitudinal axis, have different diameters, and are oriented in different radial directions relative to the longitudinal axis, the method comprising:
adjusting the insert to select the first recess or the second recess, wherein the selected recess has a diameter that is greater than a diameter of the shaft of the bone anchoring element;
inserting the bone anchoring element in the first holder such that the shaft is positioned in the selected recess;
inserting the receiving part in the second holder;
actuating the tool from a first configuration towards a second configuration to insert the head of the bone anchoring element into the receiving part; and
removing the attached bone anchoring element and receiving part from the tool.

29. The method according to claim 28, wherein the bone anchoring device further comprises a locking ring around the receiving part,
wherein when the receiving part is inserted in the second holder, the locking ring is in a first position relative to the receiving part where the head of the bone anchoring element is insertable into the receiving part, and
wherein after the head of the bone anchoring element is inserted into the receiving part, the method further comprises further actuating the tool towards the second configuration to move the locking ring to a second position relative to the receiving part, where the locking ring compresses a portion of the receiving part, such that the head cannot be removed from the receiving part and the bone anchoring element is adjustably held at a first angular position relative to the receiving part.

30. The method according to claim 28, wherein the adjusting of the insert comprises rotating the insert in the first holder to selectively access the first recess or the second recess.

* * * * *